United States Patent

Juran et al.

[11] Patent Number: 6,154,675
[45] Date of Patent: Nov. 28, 2000

[54] RESETTING ERI/POR/PIR/INDICATORS IN IMPLANTABLE MEDICAL DEVICES

[75] Inventors: Carleen J. Juran, Shoreview; James W. Busacker, St. Anthony; Michael B. Shelton, Minneapolis; Charles R. Brynelsen, North Oaks; Thomas P. Edery, Minneapolis; John D. Wahlstrand, Shoreview, all of Minn.

[73] Assignee: Medtronic, Inc., Minneapolis, Minn.

[21] Appl. No.: 09/179,773

[22] Filed: Oct. 27, 1998

[51] Int. Cl.⁷ .......................... A61N 1/362; A61N 1/378
[52] U.S. Cl. .................................. 607/29; 607/27
[58] Field of Search ........................ 607/29, 27

[56] References Cited

U.S. PATENT DOCUMENTS

| | | | |
|---|---|---|---|
| 4,231,027 | 10/1980 | Mann et al. | 340/636 |
| 4,259,639 | 3/1981 | Renirie | 324/430 |
| 4,290,429 | 9/1981 | Blaser | 128/419 PT |
| 4,324,251 | 4/1982 | Mann | 128/419 PT |
| 4,390,020 | 6/1983 | Herpes et al. | 128/419 PG |
| 4,390,022 | 6/1983 | Calfee et al. | 128/419 PG |
| 4,404,972 | 9/1983 | Gordon et al. | 128/419 PG |
| 4,437,466 | 3/1984 | Saulson et al. | 128/419 PS |
| 4,448,197 | 5/1984 | Nappholz et al. | 128/419 PT |
| 4,476,868 | 10/1984 | Thompson | 128/419 PG |
| 4,485,813 | 12/1984 | Anderson et al. | 128/675 |
| 4,743,831 | 5/1988 | Young | 320/48 |
| 4,803,987 | 2/1989 | Calfee et al. | 128/419 PG |
| 5,127,402 | 7/1992 | Mann et al. | 128/419 PT |
| 5,137,020 | 8/1992 | Wayne et al. | 128/419 PS |
| 5,350,407 | 9/1994 | McClure et al. | 607/16 |
| 5,402,070 | 3/1995 | Shelton et al. | 324/433 |
| 5,476,485 | 12/1995 | Weinberg et al. | 607/28 |
| 5,661,393 | 8/1997 | Sengupta | 320/5 |
| 5,735,882 | 4/1998 | Rottenberg et al. | 607/27 |

Primary Examiner—Carl H. Layno
Attorney, Agent, or Firm—Michael B. Atlass; Harold R. Patton

[57] ABSTRACT

An automatic, body-implantable medical device having at least two modes of operation is disclosed. The device is provided with circuitry for automatically detecting when the device has been implanted in a patient, so that the device can automatically switch from a first mode to a second mode of operation upon implantation. In one embodiment, the first mode is a power conserving mode in which one or more non-essential sub-systems of the device are disabled. Prior to detection of implant, at least two conditions of the device known to reflect whether the device has been implanted are monitored. After implant has been detected, situations in which power to the device is disrupted and then restored will cause the device to enter a predefined "power-on-reset" mode of operation. Prior to detection of implant, however, such conditions do not result in the device entering the power-on-reset mode, or this mode is reset. An Elective Replacement Indicator mode is also used which is based on measured impedance against a target battery impedance. When the measured battery impedance reaches the target level, the voltage of the battery that precipitates an ERI condition is modified.

11 Claims, 13 Drawing Sheets

RESETTING ERI/POR/PIR/INDICATORS IN IMPLANTABLE MEDICAL DEVICES

FIELD OF THE INVENTION

This invention relates generally to the field of automaticity for implantable medical device (also called IMD) systems, and more particularly to body-implantable automatic medical device systems having self aware states.

BACKGROUND OF THE INVENTION

A wide assortment of body-implantable medical devices having some level of automaticity are presently known and commercially available. The class of such devices includes cardiac pacemakers, cardiac defibrillators and cardioverters, neural stimulators and many others.

Most body-implantable devices are contained within a hermetically sealed enclosure, in order to protect the operational components of the device from the harsh in-vivo environment, as well as to protect the body from the device. Additionally, many implantable devices, operate in conjunction with one or more electrically conductive leads, adapted to conduct electrical stimulating pulses to sites within the implant patient's body, and to communicate sense signals from those sites back to the implanted device. A connector block assembly of some sort is typically used to establish the electrical connection between the lead(s) and the internal components of the device and at the same time maintain the hermetic integrity of the enclosure. Almost all current Implantable Pulse Generators (IPGs) have a hard plastic connector block mounted on a titanium hermetically sealed housing which holds the pulse generator and other circuitry and sensors. For non-IPG implantable devices which perform other medical functions, other sensors and circuits could be so housed.

Typically it is necessary to provide an automatic, body implantable device with a source of power, e.g., a battery, housed within the hermetic enclosure of the device. Battery longevity is often a critical consideration in the design and implementation of body implantable devices. It is highly impractical to replace the battery of an implanted device, and it is clearly desirable to require replacement of an implanted device—a surgical procedure—as infrequently as possible.

Because battery longevity and battery depletion are of such critical concern in relation to most implantable devices of any function, there have been numerous approaches taken for minimizing power consumption of such devices. For pacemakers, it is well-known, for example, that the pacing pulse energy content should be programmed to a level that is only as high as necessary to ensure that pacing pulses will consistently capture the patient's heart. Unnecessarily high-energy pacing pulses are wasteful of a pacemaker's power supply and hence unnecessarily reduce useful device longevity.

Another known approach to power conservation in implantable devices is to design the devices such that various electronic subsystems of the device can be independently activated (powered up) and deactivated (and powered down) as and when desired. For example, an implantable device's telemetry system need only be activated during programming sessions. This is recognized in U.S. Pat. No. 5,342,408 to de Coriolis et al., entitled "Telemetry System for an Implantable Cardiac Device." Likewise, a rate-responsive pacemaker's activity sensing and minute continuation subsystems need not be activated when the device is programmed to operate in a non-rate-responsive mode.

It should be mentioned that all references cited within this application are deemed incorporated herein by this statement of reference so as to obviate the need for redundant explanations of known art.

In an implantable device whose operation is controlled by a microprocessor, it has been recognized that power can be conserved by partially or fully deactivating, the microprocessor during intervals where no processing is necessary. Modern microprocessors, which are capable of executing potentially millions of instructions per second, can accomplish the instruction processing necessary to control an implantable device's operation in a very short time relative, for example, to the length of a typical human cardiac cycle. This means that it is not necessary for the processor to be fully active, or to be operating at its fastest possible clock speed, for a substantial portion of each cardiac cycle.

U.S. Pat. No. 4,404,972 to Gordon et al., entitled "Implantable Device With Microprocessor Control," represents one example of a prior art pacemaker which takes advantage of the processing speed of a microprocessor as compared to the length of a human cardiac cycle. In the Gordon et al. '972 reference, a pacemaker is described in which various electronic subsystems, including the pacemaker's control microprocessor, are fully activated only in response to predetermined "wake-up" events. For example, when the microprocessor completes the operating routine specified to occur following the occurrence of one event (e.g., a ventricular event), one or more wake-up events (e.g., an atrial event) is identified, and the microprocessor is deactivated. Circuitry for detecting the desired wake-up event(s) remains activated, so that upon occurrence of a wake-up event, the microprocessor and other appropriate electronic subsystems can be re-activated. However, since the microprocessor is deactivated for much of the interval between the two events, overall power consumption is reduced.

In U.S. Pat. No. 5,350,407 to McClure et al., entitled "Implantable Stimulator Having Quiescent and Active Modes of Operation," there is proposed an implantable pacemaker system in which the pulse generator is selectively operable in either a quiescent state or an active state. After manufacture of the device, the device is placed into its quiescent state, in which various sub-circuits are disabled, thereby reducing the device's power consumption prior to implant. A "wake-up" circuit continues to be operable, so that a clinician can subsequently fully reactivate the device, for example, with an activating command transmitted from an external programming unit. This arrangement is characterized as minimizing device consumption particularly during the "shelf-life" of the device, i.e., the period of time between manufacture and actual implantation of the device.

In U.S. Pat. No. 5,476,485 to Weinberg et al., entitled "Automatic Implantable Pulse Generator," there is proposed another pacemaker system that is provided with capabilities intended to minimize power consumption during the "shelf-life" of the device. The Weinberg '485 reference appears to propose a pacemaker having the capability of automatically detecting when the device has been implanted, such that prior to such detection the pacemaker can operate in a reduced power consumption mode. The implant detection is based on an assessment of lead impedance, and may also be based on an assessment of device temperature.

Notwithstanding the various measures that can be taken to minimize an implantable device's power consumption and hence maximize device longevity, battery depletion is inevitable, and pacemakers are often designed to have certain features which take this inevitability into account. For example, many pacemakers are provided with the ability to communicate an "elective replacement indicator" ("ERI") to an external programmer. The ERI informs the physician or clinician that the device's power supply is nearing, but has not yet reached end-of-life ("EOL"), the point at which the power supply cannot provide sufficient energy to keep the device operable. The advance warning provided by an ERI gives the physician the opportunity to take the appropriate measures, e.g., to replace the device, prior to EOL. Additionally, the device may automatically turn off various features processes or therapies to can serve power, responsive to the occurrence of an ERI situation. These operations can be critical for patients whose lives depend on operating their implantable devices.

It should be noted that many microprocessor patents have issued that provide many alternative power saving partial shut down and start up features, the teachings of which could be employed depending on the integrated circuit designers' needs for the implantable's microprocessor and its limitations, as well as the feature set of the implantable device.

Implantable devices also typically have an "end-of-life" or EOL function, which causes the device to enter into a special mode of operation when the device's power supply output falls below some predetermined threshold deemed to constitute the power supply's end-of-life. This special mode may be one that is less demanding on the power supply, so that at least basic functioning of the device can continue for some period of time. This may cause additional features to shut down beyond those which were shut down to conserve power for an ERI condition, or, if desired, this indicator (the EOL signal) may be the first to cause any power saving action.

Another feature commonly included in state-of-the-art implantable devices is a so-called "power-on reset" ("POR") function. POR functions typically involve placing the device into a special POR mode of operation whenever power is first applied to the device. That is, the device will begin operating in the POR mode when the power supply is first connected to the device (i.e., at the time of assembly), and at any later time when power is disrupted and then restored. The latter can occur for various reasons, including when the device is subjected to electrical noise or electro-cautery discharges, or when the battery temporarily becomes very cold, reducing the battery's output below that which is needed to maintain device operation. As will be seen in discussion later, various special functions can be automatically started responsive to a POR signal.

The cold-battery POR situation can be particularly problematic in terms of erroneously or unnecessarily putting the device into the POR mode. The most likely situation that will cause an implantable device to be triggered into its POR mode is exposure to a period of extremely low temperature while it is being shipped from the manufacturer to the customer, e.g., a doctor or hospital with a subsequent return to normal temperature. If this occurs, then the device will be operating in accordance with its POR mode (usually spare) settings, which are usually different than the preferred default settings that the manufacturer will program the device to prior to shipping to the customer. This is believed to be undesirable, as it requires the customer to (1) check every device upon receipt to determine whether it has been triggered into POR mode; and (2) reprogram those devices which have been triggered into POR mode. Additionally, POR or ERI indicators may be set or circuit timing or power settings changed due to a patient's ice-bath or sonic treatments for kidney stones, electrocautery, and being subjected to defibrillation pulses.

Other Problems During Surgery

Various other initialization issues arise during implant surgery, when an implantable device transitions to its implanted state. In the Weinberg et al. U.S. Pat. No. 5,476,485 mentioned above, as well as in Kale, U.S. Pat. No. 4,803,987; Gordon, U.S. Pat. No. 4,404,972; and Kale, U.S. Pat. No. 4,390,022, some issues related how a pacemaker should respond on implant into the body are mentioned or addressed. The applicant's invention can be applied to other implants besides pacemakers as mentioned previously. In Weinberg, for example, impedance measurements of the various pathways through which a stimulation signal may travel are taken until a satisfactory impedance value is found but not before. After finding appropriate impedance, the Weinberg pacemaker is assumed to be appropriately placed into the body or to have its electrodes properly "hooked-up" to the muscle to be stimulated, so it is programmed or made to act accordingly.

The inventors noted that in implanting devices there were a significant number of cases in which an intermittent failure of the lead, its connection to the IPG, or in connection of the lead to the body, in short, "errors in the pacing path" developed AFTER successful implant of the leads would have been established under Weinberg-like criteria. This liability could go undiscovered, allowing the physician to continue an implant surgery and close the patient before discovering the error in pacing path validity.

Accordingly, since reoperation surgery to correct a defect in pacemaker installation would be traumatic to the patient, potentially affect the reputation of the implanting physician, and possibly the perception of device quality, it would be quite helpful if the device would yield, during the implant surgery, some indication of the future validity of a pacing pathway rather than simply determining that a pacing pathway had been established. At the same time, it would also be useful to have an indication that proper lead polarity configuration had been achieved, that capture detection was satisfied and that the various sensing and sensor systems in the device were all functioning properly at the time the device detects it is implanted.

If a device were created which could accomplish all of these functions, such a device could provide additional functionality over the life of the implant including means to establish a time from which a warranty should run and means to provide an indication when the device has been explanted and reimplanted into another patient, as well as means to time limit the application of therapy deliveries, or start new ones counting time forward from the moment of implant.

Having noted that an indication of all the various states and status of the device may be useful for the surgeon during implant, it is also noted that a simple mechanism not requiring a "programmer" device to be brought into the sterile field would be useful for providing such information to the implanting surgeon.

SUMMARY OF THE INVENTION

In view of the foregoing, the present invention is directed to a method and apparatus for power conservation and power-on-reset functionality in implantable medical devices such as pacemakers, defibrillators and cardioverter/defibrillators, neurostimulators or any kind of Implantable Pulse Generator designed to stimulate the body electrically when implanted, drug pumps, iontophoretic devices and so forth.

In accordance with one embodiment of the invention, an automatic implantable medical device is provided with circuitry for automatically detecting when the device has been implanted. This detection is based upon the ongoing periodic assessment of certain conditions of the device that are known to reflect whether or not the device has been implanted.

For example, in one embodiment, circuitry in the implanted device monitors the impedance between lead terminals to determine when this impedance lies within a range consistent with device implantation. In addition, a temperature sensor in the device is used to determine when the device's temperature reaches a level consistent with implantation. In rate responsive devices, circuitry may also be included for monitoring the output of the device's activity sensor(s), pressure sensors, optical sensors or whichever sensors may be present, as well as electrical activity to determine when output consistent with patient activity, and hence with device implantation, is detected. An ECG indicator that shows that it is recording R waves, for example, or even simple marker channel information indicating that the device is implanted could be used.

In another embodiment of the invention, conditions of the device known to reflect device implantation are monitored, and when certain of these conditions are found to be consistent with implantation, such as temperature change or stabilization around body temperature, a determination is made whether these conditions persist for at least a predetermined period of time.

In accordance with another aspect of the invention, the device is provided with a Power-On-Reset (POR) function which causes the device to enter into a special mode of operation whenever power is first applied to the device and a Power Interrupt Reset (PIR) function for whenever power is disrupted and then restored to the device. The device is operative in at least two additional modes of operation, characterized as "pre-implant" and "post-implant" modes. In the pre-implant mode, the POR and PIR functions are modified for this invention as a result of being subjected to cold temperatures during shipping or other environmental conditions, so that the device retains maximum capability regardless of such conditions.

Also the ERI (Elective Replacement Indicator) function is modified to provide a multistep process with more than a single level indicator, the indicator varying based on current drain.

Additionally various embodiments of indicator means are described that enable non-programmer communications with the implanting clinician as to the status and state of the implant during implant surgery.

Further, when implant is noted, the device may use the implant time to trigger various therapy programs automatically, monitor the warranty of the device and provide an indication of prior implant history.

BRIEF DESCRIPTION OF THE DRAWINGS

The present invention is described with reference to a detailed description of a specific embodiment of the invention, when read in conjunction with the drawings in which.

DETAILED DESCRIPTION OF SPECIFIC EMBODIMENTS OF THE INVENTION

Figure 1:
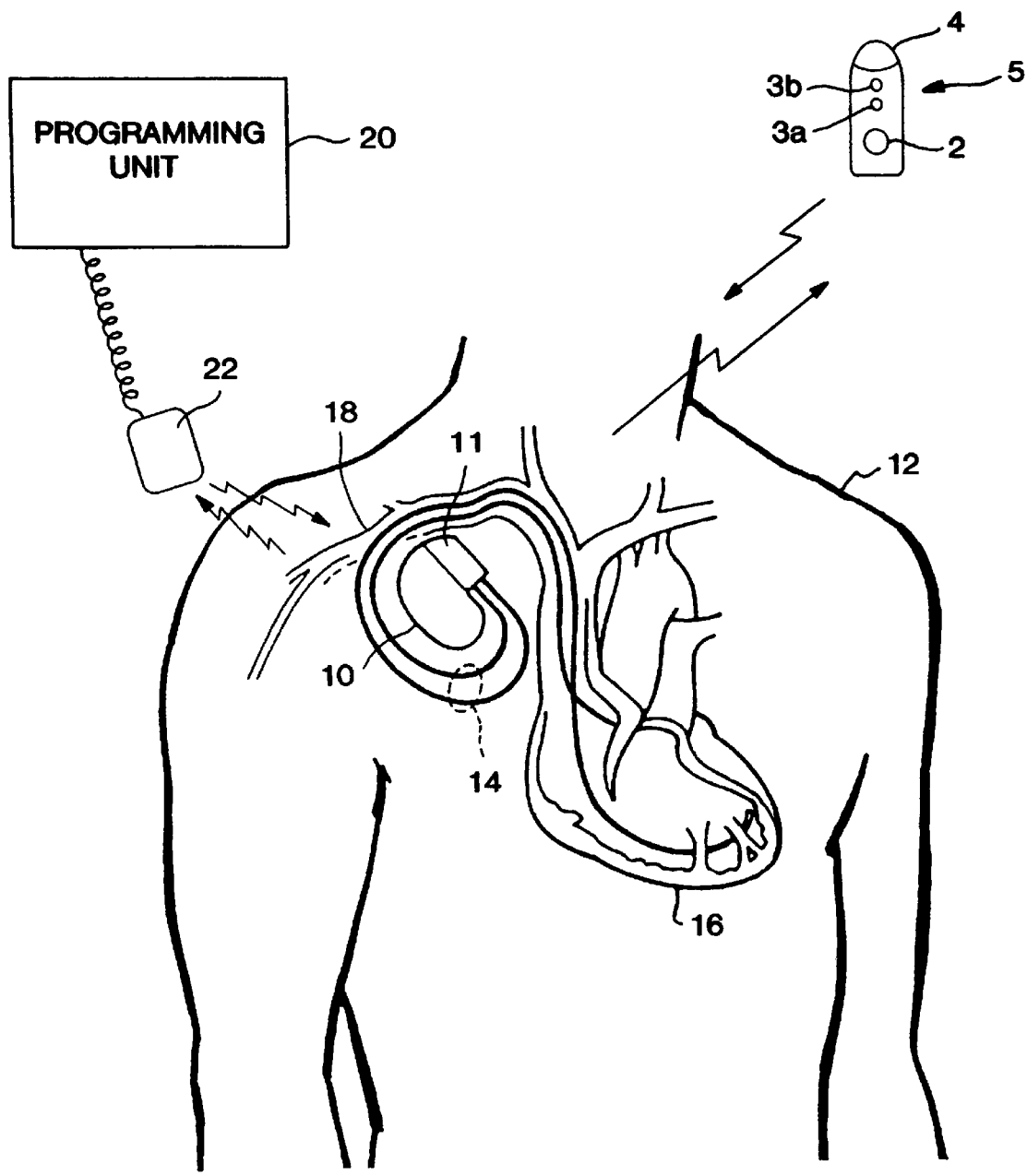
FIG. 1 illustrates an implantable device system with programmer and activator in accordance with one embodiment of the invention implanted in a patient.

FIG. 1 is an illustration of an implantable medical device system in accordance with one embodiment of the invention. The medical device system shown in FIG. 1 includes an implantable device 10—a cardiac pulse generator (commonly known as a pacemaker) in this embodiment—which has been implanted in a patient 12. In accordance with conventional practice in the art, pulse generator 10 is preferably housed within a hermetically sealed, biologically inert outer canister, which may itself be electrically conductive so as to serve as an indifferent electrode in the pulse generator's pacing/sensing circuit. One or more pacing leads, collectively identified with reference numeral 14 in FIG. 1, are electrically coupled to pulse generator 10 in a conventional manner, and extend into the patient's heart 16 via a vein 18. Disposed generally near the distal end of lead(s) 14 are one or more exposed conductive electrodes for receiving electrical cardiac signals and/or for delivering electrical pacing stimuli to heart 16. As will be appreciated by those of ordinary skill in the art, lead(s) 14 may be implanted with distal end(s) situated in either the atrium or ventricle of heart 16.

Although the present invention will be described herein in one embodiment which includes a cardiac pacemaker system, those of ordinary skill in the art having the benefit of the present disclosure will appreciate that the present invention may be advantageously practiced in connection with numerous other types of implantable medical device systems, such as those mentioned in the Summary section above.

Also depicted in FIG. 1 is an external programming unit 20 for noninvasive communication with implanted device 10 via uplink and downlink communication channels, in accordance with conventional practice in the art. Associated with programming unit 20 is a programming head 22 for facilitating telemetric communication between implanted device 10 and programmer 20. In many known implantable device systems, a programming head such as that depicted in FIG. 1 is positioned on the patient's body over the implant site of the device, such that one or more antennas within the head can send RF signals to, and receive RF signals from, an antenna disposed within the hermetic enclosure of the implanted medical device.

Also illustrated in FIG. 1 is an activator unit 5, preferably sterilizable, but having a display field here consisting of two LEDs 3a and 3b, although a strip of LEDs could be used or an LCD screen. In some embodiments, the unit 5 will not have a display, but may contain an area through which a speaker can generate sound such as area 4. Generally it will have a button 2 for activation, or it could be a simple magnet or it can have some kind of telemetry Oust downlink or both uplink and downlink capable) activatable by a button on the device surface. Its features will be explained later.

Figure 2:
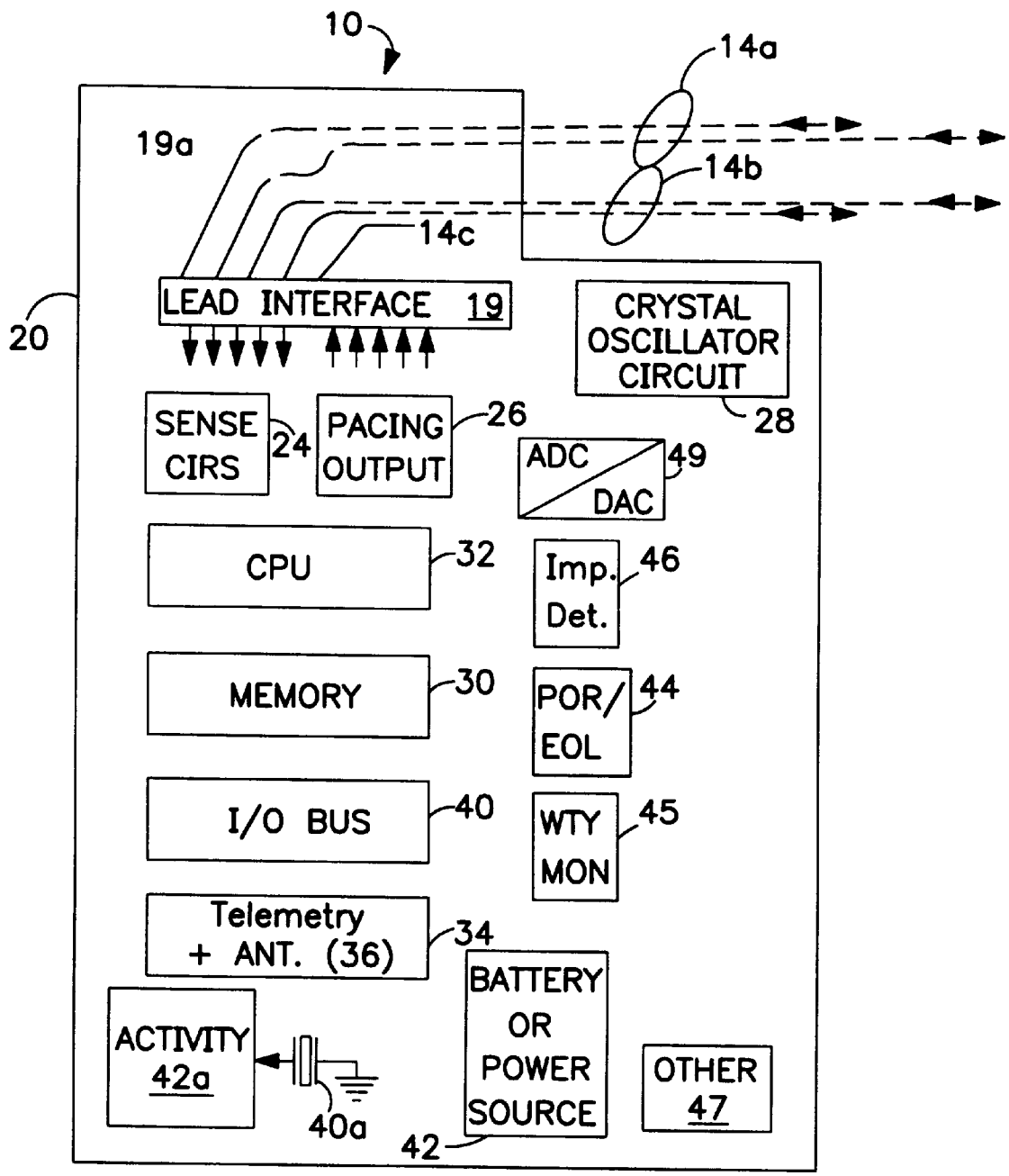
FIG. 2 is a simplified functional block diagram of the implantable device such as the device from FIG. 1.

FIG. 2 is a block diagram showing some of the various electronic subsystems which are included in pulse generator 10 in accordance with the presently disclosed embodiment of the invention. The concepts herein can be generalized to any implanted medical device (IMD), but the first and preferred application is employment in cardiac pacemakers or implantable pulse generators. As can be seen from FIG. 2, pulse generator 10 comprises a primary stimulation control circuit 20 for controlling the device's pacing and sensing functions. The circuitry associated with stimulation control circuit 20 may be of conventional design, in accordance, for example, with the disclosure of U.S. Pat. No. 5,052,388 to Sivula et al., entitled "Method and Apparatus for Implementing Activity Sensing in a Pulse Generator," or of U.S. Pat. No. 5,271,395 to Wahlstrand et al. entitled "Method and Apparatus for Rate-Responsive Cardiac Pacing." The Sivula et al. '388 and et al. '395 patents are each hereby incorporated by reference herein in their respective entireties.

To the extent that certain components of pulse generator 10 are conventional in their design and operation, such components will not be described herein in detail, as it is believed that design and implementation of such components would be a matter of routine engineering to those of ordinary skill in the art. For example, stimulation control circuit 20 in FIG. 2 includes sense amplifier circuitry 24, stimulating pulse output circuitry 26, a crystal clock 28, a random-access memory and read-only memory (RAM/ROM) unit 30, a central processing unit (CPU) 32, and an internal communication (telemetry) circuit 34 for facilitating communication with external programmer/control unit 20. All of these certain components are well-known.

With continued reference to FIG. 2, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional. connector block assembly 11, shown in FIG. 1 but not shown in FIG. 2. Electrically, the coupling of the conductors of leads and internal electrical components of pulse generator 10, is facilitated by means of a lead interface circuit 19 which functions, in a multiplexor-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 2, although it will be clear to those of ordinary skill in the art that, for example, leads 14 will at times be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14.

As previously noted, stimulation control circuit 20 includes central processing unit 32 which may be an off-the-shelf programmable microprocessor or microcontroller, but in the presently preferred embodiment of the invention is a custom integrated circuit. (Those of ordinary skill in the art will appreciate that another alternative would be for pacemaker 10 to be controlled not by a processor, but by means of custom circuitry implementing a state-machine type of operational control. It is believed that persons of ordinary skill in the art having the benefit of the present disclosure would be able to readily adapt the presently disclosed embodiment to a state-machine based system.)

Although specific connections between CPU 32 and other components of stimulation control circuit 20 are not shown in FIG. 2, it will be apparent to those of ordinary skill in the art that CPU 32 functions to control the timed operation of stimulating pulse output circuit 26 and sense amplifier circuit 24 under control of a process operating the microprocessor and constructed by programming (i.e. a "program") stored in RAM/ROM unit 30. These processes are responsive to signals from sense amplifier circuitry 24 and activity sensing circuitry 42a, the output of which are converted to digital signals and checked by the controlling processes. Those of ordinary skill in the art will be familiar with how to easily implement such an operative arrangement.

With continued reference to FIG. 2, crystal oscillator circuit 28, in the presently preferred embodiment a 32,768-Hz crystal controlled oscillator, provides main timing clock signals to stimulation control circuit 20. Again, the lines over which such clocking signals are provided to the various timed components of pulse generator 10 (e.g., microprocessor 32) are omitted from FIG. 2 for clarity.

It is to be understood that the various components of pulse generator 10 depicted in FIG. 2 are powered by means of a power supply, such as a battery (not shown separately, but in box 42) which is contained within the hermetic enclosure of pacemaker 10, in accordance with common practice in the art. For clarity in the FIGS., the battery or power source 42 is drawn as a simple box, and the connections between it and the other components of pulse generator 10 are not shown. (Some implantable devices may be powered by sources other than battery power. For such devices the teachings of this disclosure not related to battery power may also be useful. On the other hand, the motive force may be lost for a capacitive charging system for long enough to run the charge out below a critical level. In such cases, the functions described could be easily implemented for such an arrangement in such systems using large slow discharge capacitive systems without batteries.)

Stimulating pulse output circuit 26, which functions to generate cardiac stimuli under control of pacing trigger signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits which would be suitable for the purposes of practicing the present invention.

Sense amplifier circuit 24, which is of conventional design, functions to receive electrical cardiac signals from leads 14 and to process such signals to derive event signals reflecting the occurrence of specific cardiac electrical events, including atrial contractions (P-waves) and ventricular contractions (R-waves). These event-indicating signals are provided to CPU 32 for use in controlling the synchronous stimulating operations of pulse generator 10 in accordance with common practice in the art. In addition, these event indicating signals may be communicated, via uplink transmission, to external programming unit 20 for visual display to a physician or clinician.

FIG. 2 shows that pulse generator 10 also includes an activity sensor 40a, coupled to activity sensing circuitry 42a. Sensor 40, which in the presently disclosed embodiment of the invention is a piezoelectric transducer or the like, provides to activity sensing circuitry 42a an electrical signal reflecting the level of the pacemaker patent's activity level. Activity sensing circuit processes (e.g., filters) the activity signal and provides it (or a digital quantification of it) to CPU 32, such that the patient's activity level may be among those factors relied upon by pulse generator 10 in operating in accordance with the desired pacing algorithm. A pacemaker system which employs a piezoelectric activity sensor and associated circuitry suitable for the purposes of practicing the present invention is described in more detail in U.S. Pat. No. 4,485,813 to Anderson et al., which patent is hereby incorporated by reference herein in its entirety.

Additional sensors could be employed as was suggested in the Summary of the Invention. An optical sensor may be mounted in the connector block or on the surface of the device or it's leads tuned to notice the red frequencies present in blood, for example, and such a sensor could then generate a signal indicating implant. Alternatively or additionally, the surgeon could provide a tuned light source to provide an additional indicator. A sound sensor could look for patterns of auditory vibrations occurring within the range and of the frequency expected for heart beats. In the case of a pacemaker or cardioverter defibrillator or any device with electrodes checking electrical activity of the heart, (in contact with it or merely arranged on a device implanted far from the heart) this electrical activity could fall within an expected range of frequency and amplitude to provide another indicator of implant. Impedance pulses currently used by some pacemakers to measure breathing activity could provide another. Temperature and pressure sensors may provide further signals to indicate implant. Such sensors and circuits could be included in the box 47, for example. Further the device being implanted could be something other than a pacemaker and any other features needed by such IMDs could be included in box 47 as well.

The implantable pulse generator or other IMD further includes a power-on-reset ("POR") and end-of life ("EOL") indicator circuit 44. In accordance with known practice in the art, POR/EOL circuit 44 includes voltage and/or current level detection circuitry for assessing the energy output of the pulse generator's power supply, so that pulse generator 32, under control of CPU 32, can take appropriate steps in the event that the power supply becomes depleted or power is interrupted, as discussed above.

Finally, FIG. 2 shows that, in accordance with one aspect of the invention, pulse generator 10 includes an implant detect circuit 46. As will be hereinafter described in further detail, implant detect circuit 46 functions to automatically determine, based on input from various sensors and other circuitry associated with pulse generator 10, when pulse generator 10 is implanted in a patient, and to provide an indication of this event to CPU 32.

Those of ordinary skill in the art will appreciate that pulse generator 10 may include numerous other components and subsystems not specifically shown in FIG. 2. For example, pulse generator 10 may include other types of physiologic sensors and associated circuitry, backup or redundant control circuitry, self-diagnostic circuitry, defibrillator circuitry, drug pump delivery circuitry, and so forth. Applying the invention herein to other implantable medical device including drug pumps and neural stimulators, additional sensors and measurements may be taken to indicate implant. To the extent that such additional components or subsystems are not discussed herein, it is believed that their presence or absence in pacemaker or IMD 10 is not relevant or necessary for an understanding of the present invention.

In conventional pacemaker systems, normal operation of pacemaker 10 is carried out under control of CPU 32, based primarily upon: (1) control programming stored in RAM/ROM unit 30; (2) programmed operational parameter values, selected by the programming clinician and also stored RAM/ROM unit 30 or on-board CPU registers; (3) input signals from sense amplifier circuitry 24 reflecting the detected occurrence of intrinsic cardiac electrical activity; and (4) input signals from other sensors, such as activity sensing circuitry 42 and implant detect circuitry 46, which reflect certain physiologic conditions of the patient and conditions of pulse generator 10 itself. The control programming and the programmed operational parameter values essentially define many aspects the pacing algorithm, in that they can determine the pacemaker's behavior given a particular combination of sense amplifier and sensor signals.

Moreover, pulse generator 10 in accordance with the presently disclosed embodiment of the invention is multi-programmable; that is, RAM/ROM unit 30 stores control programming defining more than one operational algorithm for pulse generator 10, so that, as instructed by external programmer 20, CPU 32 can control pulse generator 10 to selectively operate in any of a plurality of operational modes. As is described below, many variations on the set of features and programs operative in the IPG 10 may be automatically set.

RAM/ROM unit 30 may store control programming corresponding to any or all of the well-known pacing modes DDD, DDDR, DDIR, DDI, DVIR, DVI, VVIR, VVI, etc. RAM/ROM unit 30 may also store control programming for other modes, for example, an asynchronous "magnet mode" in which the pacemaker operates when a magnet is placed over the implant site, in accord with well-known pacemaker design. In one aspect of the embodiment of the invention, pulse generator 10 may be operable in one or more quiescent or low-power modes in which selected ones of the various electronic sub-systems and operating programs and therapy features of the medical device 10 can be disabled or deactivated, in order to conserve the device's power during periods of time (e.g., during a device's "shelf-life") when such sub-systems, programs, and features are not needed.

It is noted that only one block is designated for an Analog to Digital converter. With the wide variation available in design and additional features for sensing and providing therapy, it is simply noted that since most processing is digital, some conversion circuitry is required if digital circuits are used, such as the RAM/ROM and microprocessor circuits, and that in certain devices the circuit or circuits performing this function may provide Digital to Analog conversions also.

Those of ordinary skill in the art will appreciate how deactivation of selectable, individual electronic sub-systems and features of pulse generator 10 can be achieved depending upon the current mode or state of the implantable medical device 10. For example, it may be desired in a non-rate-response mode to deactivate activity sensing circuit 42 to conserve power. This can be accomplished by a control signal issued by CPU 32 to a de-coupling transistor or switch interposed between activity sensing circuitry 42a and its power supply. If the IPG 10 uses an impedance measuring circuit for minute ventilation, that too may be disabled. The particular manner in which various subsystems are deactivated is not believed to be critical to an understanding of the present invention, and it is believed that those of ordinary skill in the circuit art could readily implement such functionality to accommodate the particulars of the implanted medical device they may be employing.

In the presently preferred embodiment of the invention, implant detect circuit 46 includes circuitry for monitoring at least two conditions of pulse generator 10 that are known to reflect whether or not pulse generator 10 has been implanted into a patient. One such condition is lead impedance. When no lead is connected to pulse generator 10, or if the lead electrodes are not disposed in the heart, lead impedance will be very high, reflecting an essentially open circuit between the electrodes. Once properly implanted, however, the lead impedance will drop to a notably lower level, in the range of 2000 ohms or less. This change can be readily detected by implant detection circuit 46. Impedance measuring circuits for implantable medical devices are well known in the art. One U.S. patent that describes this lead impedance measurement circuitry is U.S. Pat. No. 5,534,018 to Wahlstrand et al., entitled "Automatic Lead Recognition for Implantable Medical Device," which is hereby incorporated by reference herein in its entirety. Alternate circuits for this function are known as well as the ones described in the '018 patent, and those may also be used.

Another condition that may be monitored by implant detect circuit 46 in the presently disclosed embodiment of the invention is temperature. For this purpose, a, temperature sensor, such as the solid-state LM34, LM35, LM135, LM235, or LM335 series of integrated circuit temperature sensors commercially available from National Semiconductor Corporation, Santa Clara, Calif., can be included in implant detect circuit 46. Alternatively a temperature circuit may be implanted on the Integrated Circuit with other sensor and control circuits in a manner known in the art. The temperature monitoring circuitry preferably detects when the temperature of pulse generator 10 reaches, nears or is on a suitable vector to achieve human body temperature. For example, the temperature monitoring circuitry could indicate to circuit 46 when the temperature of pulse generator falls within a range of a few degrees of body temperature.

Still another condition of pulse generator 10 that is preferably monitored by implant detect circuit 46 is the activity sensor output. As noted above, pulse generator 10 preferably includes a microphone-like piezoelectric transducer (often referred to as an activity crystal) for detecting physical activity of the implant patient, or single or multi-axis accelerometers in accordance with known pacemaker technology. (Of course, one may substitute the newer micromachined vibrating beam or bridge accelerometers is desired too.).The output of activity sensing circuitry 42a is a signal whose level (in either an analog or a digital sense, depending upon the implementation) reflects patient activity. Accordingly, this signal may be provided to implant detect circuit 46 so that it can be monitored. When the activity signal begins to met predefined criteria consistent with patient activity, this can be used as an indication that pulse generator 10 has been implanted. A particular set of movements taught to an implant surgeon could be used as well and perhaps more reliably than programming to detect movement characteristic of implant surgery.

Figure 3:
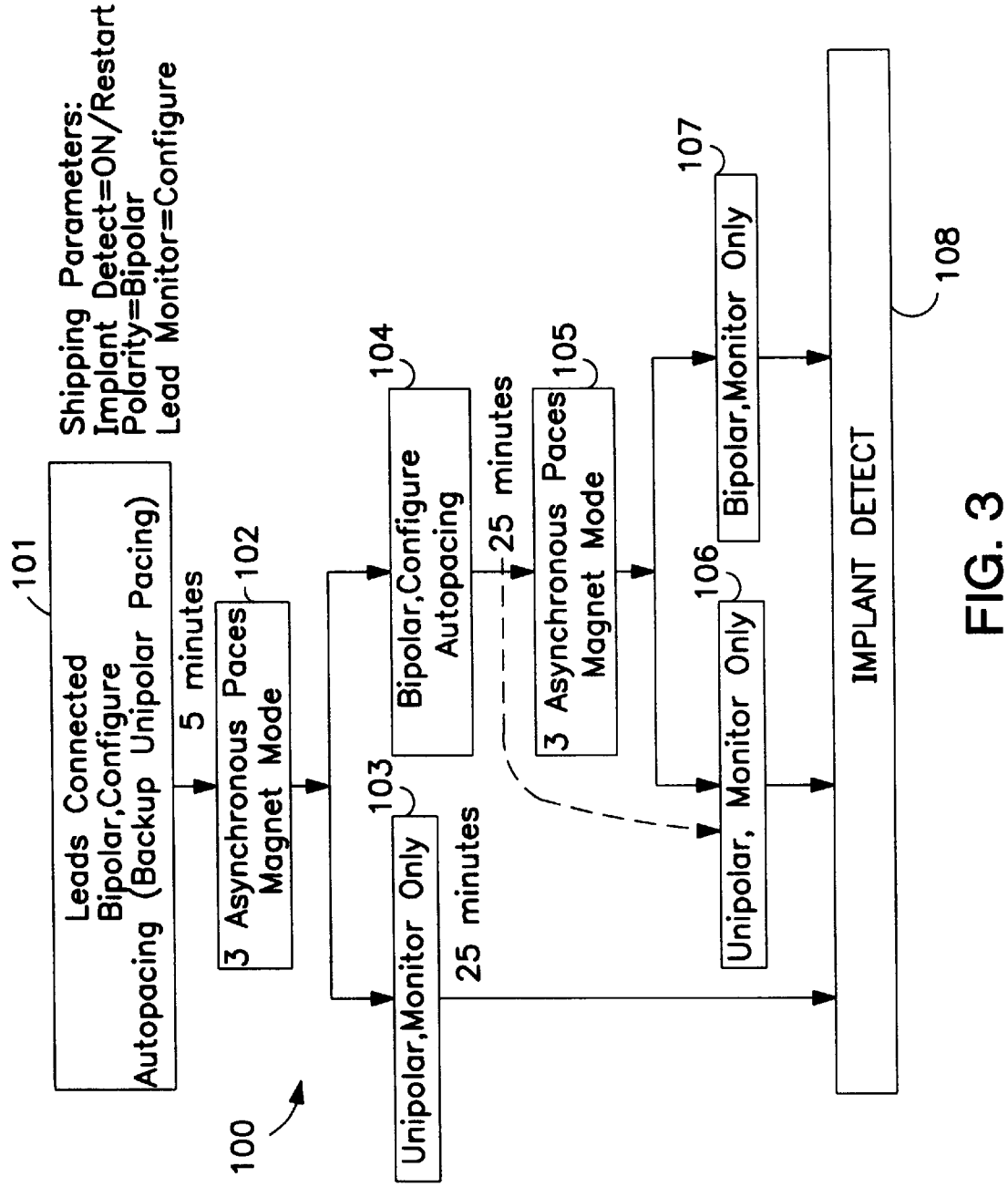
FIG. 3 is a flow diagram illustrating implant detection functionality of the device from FIG. 2.

Referring now to FIG. 3, a flow diagram illustrating operation of pulse generator 10 in accordance with the presently disclosed embodiment of the invention are shown. It will be appreciated by those of ordinary skill in the art that this flow diagrams may be implemented in a variety of ways, depending, for example, upon whether pulse generator is microprocessor based or based on custom integrated logic and time circuitry, state machine circuitry, or the like.

Various other sensors and subsystems may also be used to detect implant for example an optical sensor tuned to detect the presence of blood, mounted for example on the exterior of an implantable device would give an indication of implant once the device was in the body.

Finally, an exterior influence such as a magnetic field or RF stimulation provided by a device used in the operating room would give a Physician-activated indication of the time of implant. Alternatively, the Physician can query the implant through telemetry or other signaling technique to report out the time it is setting internally as the implant time.

FIG. 3 illustrates operation 100 of an IMD such as pacemaker 10 of FIG. 2, as it relates to implant detection in accordance with a presently disclosed embodiment.

Part of the pre-implant mode of operation involves implant detection, which may involve periodic assessment of at least two conditions of pulse generator 10 indicative of device implantation. This assessment is performed by implant detect circuit 46. As noted above, one of these conditions is lead impedance. In the pre-implant mode, CPU 32 periodically checks the outputs of implant detect circuit 46 to determine whether implant has occurred. The frequency of these checks may vary from implementation to implementation. For example, they may occur many times a second, or once per second, or once per minute; this is a design consideration that can be left to the IMD designer. Alternatively, they may remain "off" until an external signal sent by the implant surgery team is received by the device which only then checks for implant. In any event they will not begin until the device is receiving battery energy above the PIR level.

Also, the nature of the "output" of the implant detect circuit may vary from implementation to implementation. For example, one implant detect circuit 46 may contain a register, addressable by CPU 32, whose digital contents indicate whether or not and possibly when, certain implant detection criteria have been met. Alternatively, implant detect circuit 46 might output one or more analog signals whose levels reflect whether implant detection criteria have been met. Again, it is believed that these implementation details are not relevant to the present disclosure and can be left to the discretion of the implantable device or IPG designer.

In general the first step 101 is to determine that the leads are connected and to see what the configuration of the leads is.

FIG. 3 indicates that the lead impedance check is periodically made until the lead impedance is found to have fallen below the threshold value. While a temperature sensor could be used, it is preferred to save the space, power and complexity by counting out a period of time, here 5 minutes after the lead connectedness is found by impedance testing and initialization of the pacing pulses before issuing the asynchronous pace pulse test of step 102. The goal of the process of FIG. 3 is to determine whether and what leads are connected. The intent of using this time component is to allow the physician to connect-disconnect and reconnect the leads from the IPG during the surgery. I.e., he gets to change his mind as needed in case he connected the wrong lead (for example, switched the Atrial and Ventricular connections to the pacemaker or other IPG), or needs to reposition the lead (if it is not properly situate in association with the tissue to be stimulated), or for some other reason needs to temporarily connect the leads to the PSA (Pacing System Analyzer). Similar time periods could be used but we have settled on the ones disclosed here as preferred for our invention. The sequence of events takes one 30 minute unit of time if all goes well but can be restarted. The lead polarity may be configured as may be the rate response, sensing assurance, capture management and also any diagnostic or therapeutic features can be tested during this time, or later if desired. To "monitor" the leads means to recognize the polarity and pace accordingly. This function may also be called a "monitor switch" mode in the art. The pacemaker continuously monitors the integrity of the attached leads using the pacing pulse or separate impedance testing pulses as is known in the art. Impedance measurements that indicate a failing bipolar lead may cause an automatic switch to unipolar configuration using the monitor function. In accord with U.S. Pat. No. 5,897,577 issued Apr. 27, 1999, and U.S. Pat. No. 5,910,156 issued Jun. 8, 1999, both to Cinbus et al., and incorporated hereinto by this reference, we can capture data on open and short circuit paces to record this data to assess lead integrity over any period of time. The 'autopace' function also relies on checking bipolar circuit pace., for open circuit pacing. If the device discovers an open circuit pace in bipolar configuration, a unipolar pace can be delivered within a short time (less than 130 usecs) from the original bipolar pace attempt. A second pace would not be appropriate after a short circuit pace.

In the preferred embodiment we use 5 minutes but other times could be selected, after the leads are connected and the device is placed. If the impedance of two of the 3 paces at a magnet rate (85 ppm) indicates unipolar polarity, the device will set the pace polarity to unipolar and the lead monitor to monitor only. If the impedance of 2 of the three paces indicates bipolar polarity, the device will continue to monitor the pace polarity with autopacing enabled. We call this monitoring with autopacing enabled a "configuration mode." Preferably when the device establishes unipolarity, the polarity will remain unipolar and not revert to bipolarity. However if an open circuit pace is detected on a lead during the whole implant testing time, here 30 minutes, the 30 minute period will automatically be restarted and the pace polarity for that lead only will be set back to bipolar.

If during the remaining 25 minutes, the impedance of half of the most recent paces indicates unipolar polarity, (i.e., impedance of unipolar pace in range but of bipolar pace is out of range, the pacemaker will set the pace polarity to unipolar and the lead monitor to monitor only.

This sequence is illustrated in the flow chart, with the delivery of the 3 asynchronous paces defining the first setting of steps 103 or 104 and the rechecking step 105 in bipolar mode confirming or shifting to unipolar pacing in steps 106 or 107. Step 105 is always required to confirm bipolar versus unipolar configurations. Step 107 will be skipped and the device will stay in autopacing if the device is programmed to be adaptive. However if after the 5 minute period is complete and the bipolar configuration and autopacing is set in 104, the device will constantly be checking the impedance of the lead circuits. If (in the preferred embodiment) 8 of 16 paces indicates unipolar configuration, the device will transition to step 106, and pace in unipolar mode, monitor only before going to step 108. On the other hand, if the bipolar configuration continues and the step 105 recheck occurs without there being 8 of 16 unipolar pulse impedance measurements during the 25 minutes remaining in the total 30 minute implant detect period, the device will transition to step 107 before moving to step 108.

At the conclusion of this exercise the status of the implant detect can be generated and stored or reported out over whatever system is in place to display the information to the implanter at step 108. Basically, what we have accomplished with this system is to assure that a level of implant stability has been achieved before reporting out or to whatever relevant subsystems depend upon it, an indicator of implant stability.

It is to be understood that FIG. 3 is merely an illustrative example of device operation in accordance with the presently disclosed embodiment of the invention. It is contemplated that various alternative implementations may be realized. For example, in the example of FIG. 3, the three conditions assessed by implant detect circuit 46 are essentially prioritized, in that only after the lead impedance criteria have been met will temperature be assessed, and likewise only after the temperature criteria have been met will activity sensor output be assessed. This prioritization is not necessary for the purposes of the present invention. In an alternate embodiment, all conditions could be periodically be checked; this might be done to take into account the possibility that one (or more) of the sub-circuits in implant detect circuit 46 is not working properly and hence falsely indicates that pulse generator 10 had not been implanted.

Also, it is contemplated that more, or fewer, conditions known to reflect device implantation can be included in the implant detection algorithm, and it is believed that those of ordinary skill in the art will be readily able to adapt the flow diagram of FIG. 3 to include more or fewer tests. For example, the outputs from other physiologic sensors (oxygen, pressure, etc.) which may be in device 10 or attached to it by leads may be assessed to determine whether implant has occurred.

It is contemplated that with any implementation of the present invention, in addition to the automatic implant detection capability described herein, provision may be made for this implant detection feature to be overridden by programming commands. This would enable a programming physician or clinician to put pulse generator 10 into a fully operative condition without reliance upon the automatic implant detection capability of the device.

In general the operation of the device in step 101 to test lead validity can be as follows. DC impedance measurements of the tip-ring (bipolar) and tip-case (unipolar) pacing paths will be performed in both chambers once per second, or in the most preferred embodiment, once per pace output, i.e., it is done on every pace. This is enabled at final IPG test and continues through the completion of the implant complete interval here described also as the 30 minute interval.

At least thirty (30) seconds (or in our most preferred embodiment, we keep a buffer of the impedance of the last 16 paces) of these values are stored on a rolling basis. the decision as to which paths are valid will be made by comparing these values. If any of these values are out of range for a given path (bipolar or unipolar) that path is not considered valid. If all the values are in range, the path will be considered valid. The results of this test may be obtained in one of two ways. First, the result of the test will be automatically provided as soon as a valid unipolar path is seen.

In, for example, at least one minute of data collected the results will be provided about one minute (or 16 paces) after the pacemaker is inserted into the body. (Since the unipolar path requires the presence of the case electrode, this is a requirement for a valid unipolar path. There cannot be any valid impedance measurement data for this path without the case and a connected lead being implanted.)

For the second way, the test results may be requested using an external instrument that communicates with the pacemaker via an infrared link or limited code RF pulse similar to the remote for an automobile keyless entry system. When the pacemaker received the trigger from the instrument, it will acknowledge receipt of the trigger as indicated in the table below and then begin collecting at least about 30 seconds of data. At the completion of this time period, the results of the test will be provided. Notification of results can be made by any of the following alternate embodiments:

Green or Amber LED either by the implant or by the triggering device when it received an A.O.K. (all O.K.) message from the implant that is illuminated for 30 sec.

and/or indicator in connector block that changes color due to applied electrical signal (LCD).

These embodiments will be used as follows:

| Message to be conveyed | Sound | LED | LCD |
|---|---|---|---|
| All unipolar paths are not valid | Low tone/ speech | Amber | Color 1 |
| Unipolar paths valid, 1 bipolar valid | Single chirp/ speech | Green | Color 2 |
| Unipolar paths valid, 2 bipolar valid | Two chirps/ speech | Green Flashes and then remains illuminated | "Flashes color 2" and then remains illuminated |
| Acknowledgment of Trigger | Single chirp/ speech | Flashes Green | Flashes |

It should be noted that a voiced encoded chip may be used to speak one or more of the messages to be conveyed in a convenient language, if preferred. This collection of function and procedures will permit the pre-implant detection and indication of electrical validity of the pacing path so as to save the patient a new surgery when it can be prevented.

It should also be noted that the device being implanted can simply perform the automatic functions without reporting out the implant status if desired.

Figure 4A:
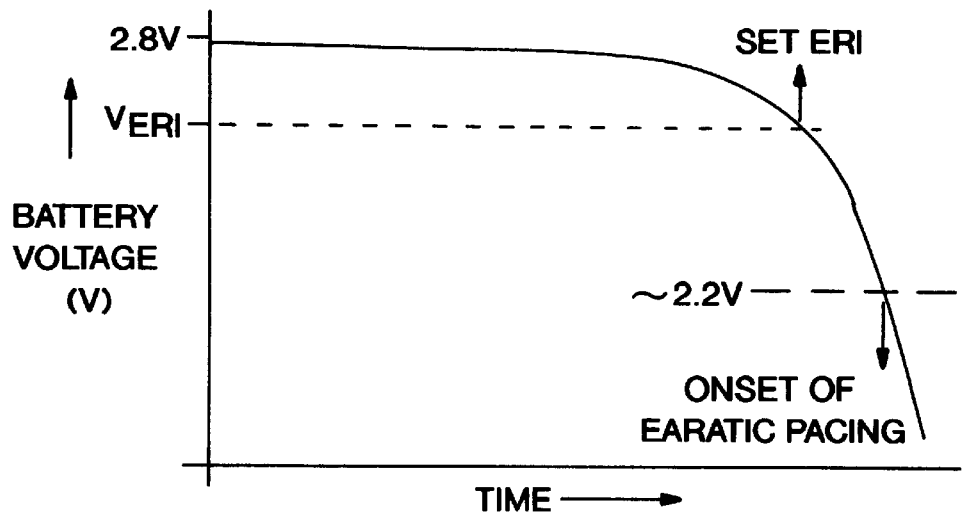
FIGS. 4a–d are graphs, having voltage on each vertical axis and for 4a, time, for 4b and 4c, discharged capacity and for 4d, battery impedance along the horizontal axes.
Figure 4B:
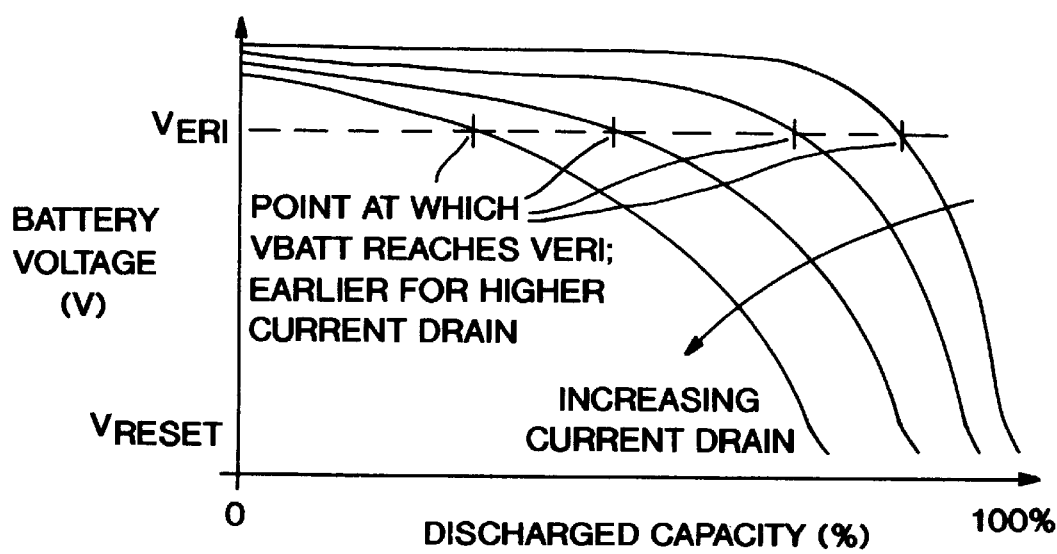
Figure 4C:
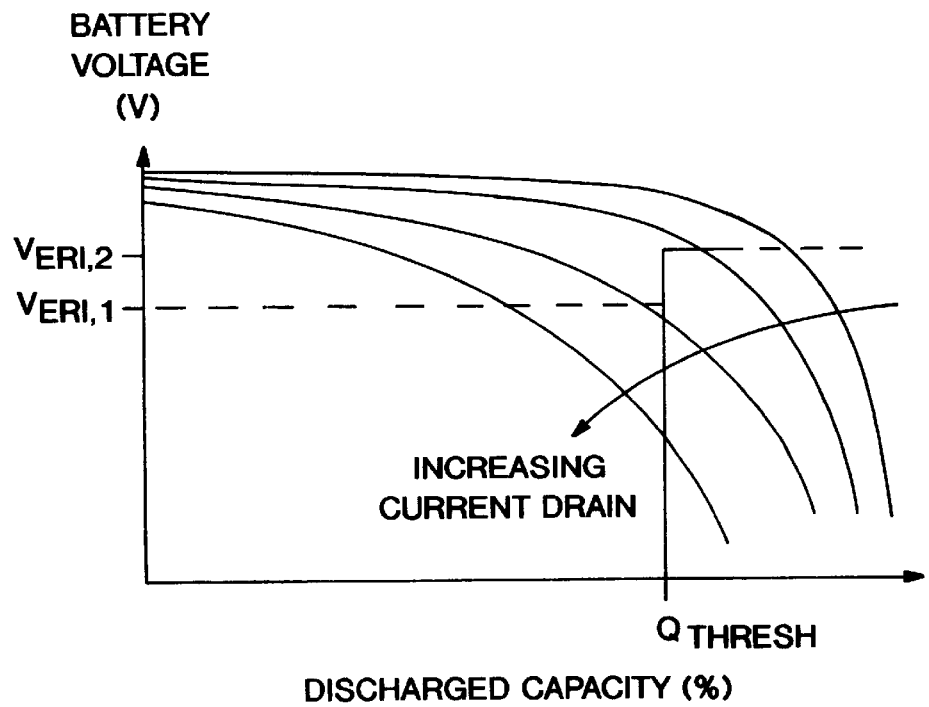
Figure 4D:
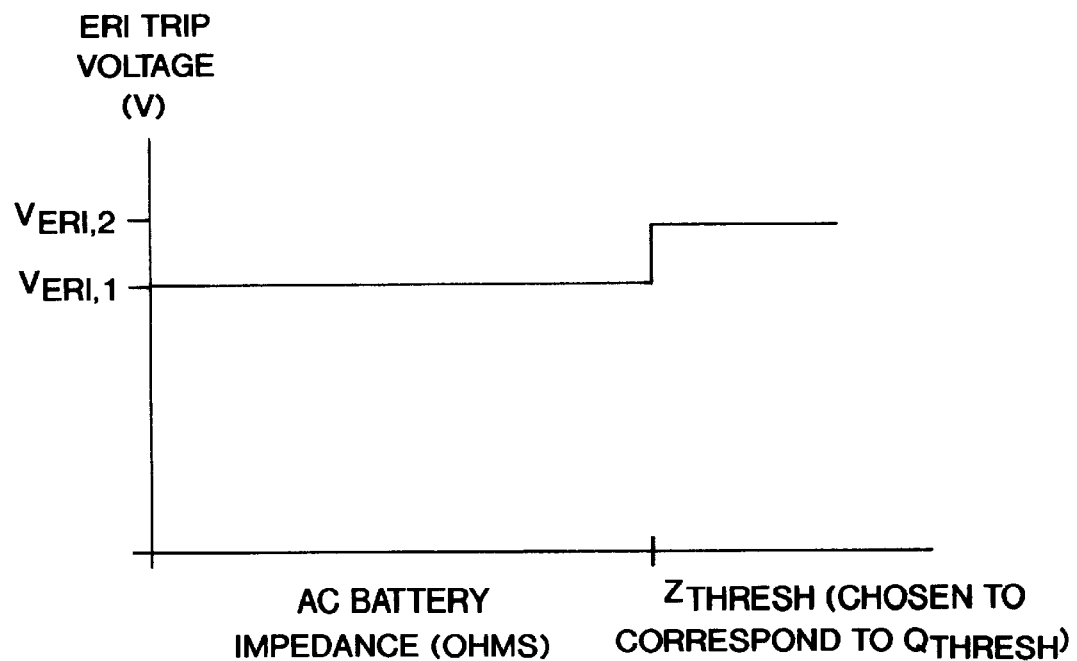
Figure 5:
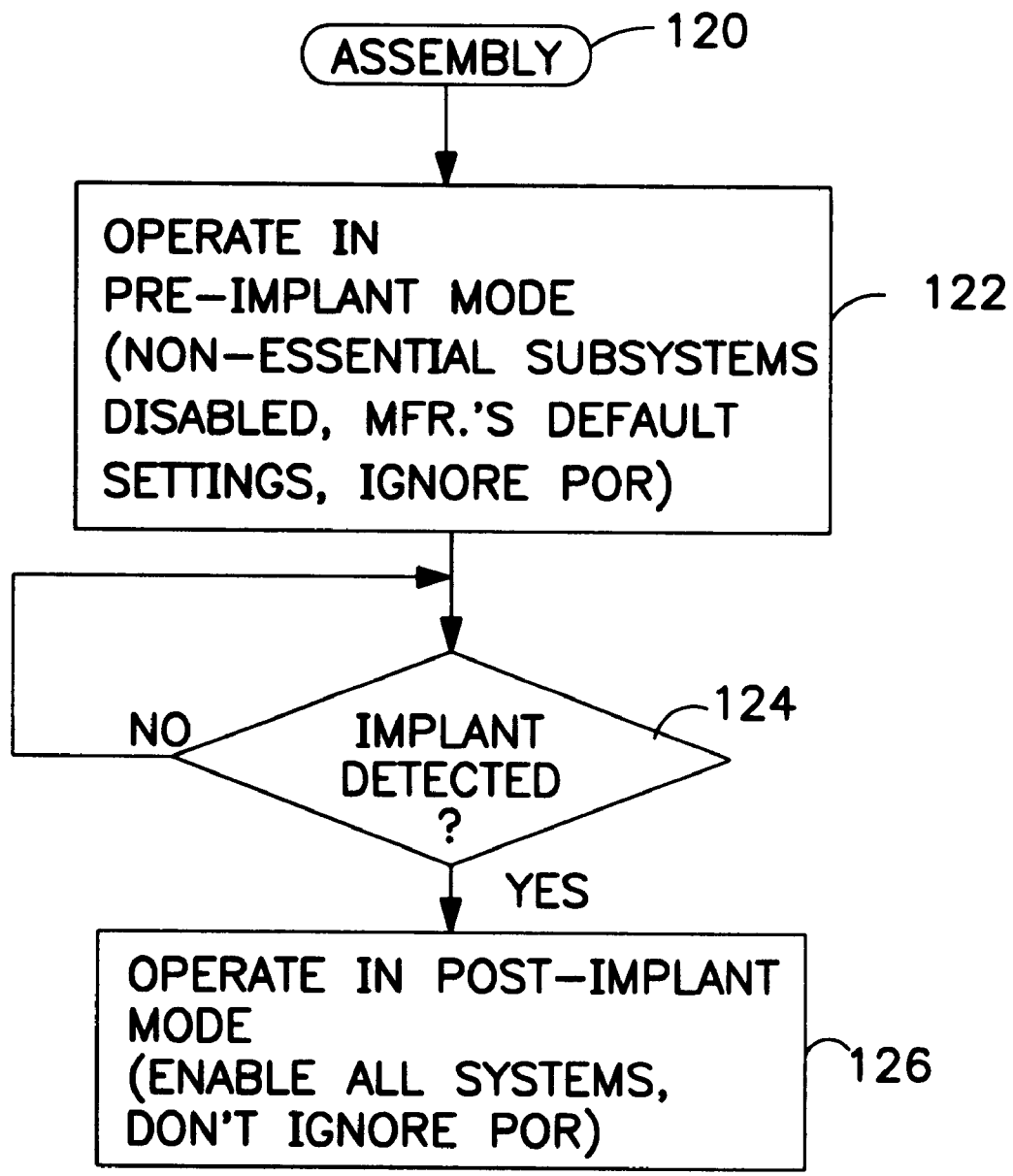
FIG. 5 is a flow diagram illustrating power-on-reset functionality of the device from FIG. 2.

Turning now to FIG. 5, operation of pulse generator 10 as it relates to the device's power-on-reset ("POR") function will be described. Like FIGS. 3 and 4, the flow diagram of FIG. 5 begins with assembly of pulse generator 10, as represented by block 120. Upon assembly, pulse generator 10 begins operating in a "pre-implant" mode. As indicated in block 122, the pre-implant mode is a mode in which certain non-essential sub-systems of pulse generator 10 are deactivated or disabled. Such "non-essential" systems may include, for example, the implantable pulse generator's telemetry circuit 34, sense amplifier circuit 24, and pacing output circuit 26. In our preferred embodiments, the sense amplifier will remain enabled.

To the extent that the relevant sub-systems of pulse generator 10 are not disabled in the pre-implant mode, CPU 32 operates pulse generator 10 in accordance with the manufacturer's default programmable parameter settings. Also, in accordance with one aspect of the presently disclosed embodiment of the invention, conditions which would otherwise cause the device to enter into the power-on-reset ("POR") mode of operation are ignored. That is, if power to the electronic components of pulse generator 10 is temporarily disrupted for some reason, then when power is restored, the device will continue to operate in accordance with the manufacturer's default programmable settings, rather than the settings corresponding to the device's POR mode of operation.

During operation in the pre-implant mode, pulse generator 10 carries out the implant detection routine described above with reference to FIG. 3. This is represented by block 124 in FIG. 5. So long as implant is not detected, operation will continue in the pre-implant mode.

For a number of unrelated reasons the POR/PIR status in modern pacemakers has become fairly complex and it is believed that a short exposition on some of these complexities is necessary for a full understanding of the invention Because non-volatile RAM takes up more space on an integrated circuit than dynamic or other RAM memory types, very little information is stored when the battery power is gone or less than satisfactory, since it is stored in the less volatile RAM and there is less of it than the regular memory circuits used in the implant's integrated circuitry. If the device has been programmed with therapy features or parameter settings prior to implant, a register in the less volatile RAM (NVRAM or LVRAM) stores a signal representing this, and a different signal value if not. In this way, after a POR/PIR occurs the implant will "know" whether to consider the data related to programming as valid instead of looking for new data and programming (while retaining factory basic settings for emergency operation such as VVI mode for a pacemaker, and nominal settings for Input/ Output values). After a POR/PIR too, the implant (or IPG) has to determine if it is implanted or not, so as to determine whether to activate therapy feature programs and housekeeping functions for maintaining itself within the body of a patient. This is done by checking another memory register that holds either a value indicating implanted or one indicating not implanted.

If and when implantation is detected, operational flow proceeds to block 126 in FIG. 5, wherein the device begins to operate in a "post-implant" mode. In the post-implant mode, all systems are fully operational, and operation proceeds in accordance with the device's programmed parameters, which may be either the manufacturer's default programmed settings, or programmed settings established by the implanting physician. In either case, however, post-implant situations which indicate that power to the device has been interrupted and restored will cause the device to enter into the POR/PIR modes. That is, unlike the pre-implant mode, POR/PIR conditions are not ignored post-implant. Therefore, by ignoring POR/PIR conditions pre-implant, it is unlikely that the device will be in a POR/PIR mode upon delivery to a patient as a result of the device having been subjected to cold temperatures during shipping.

Figure 6:
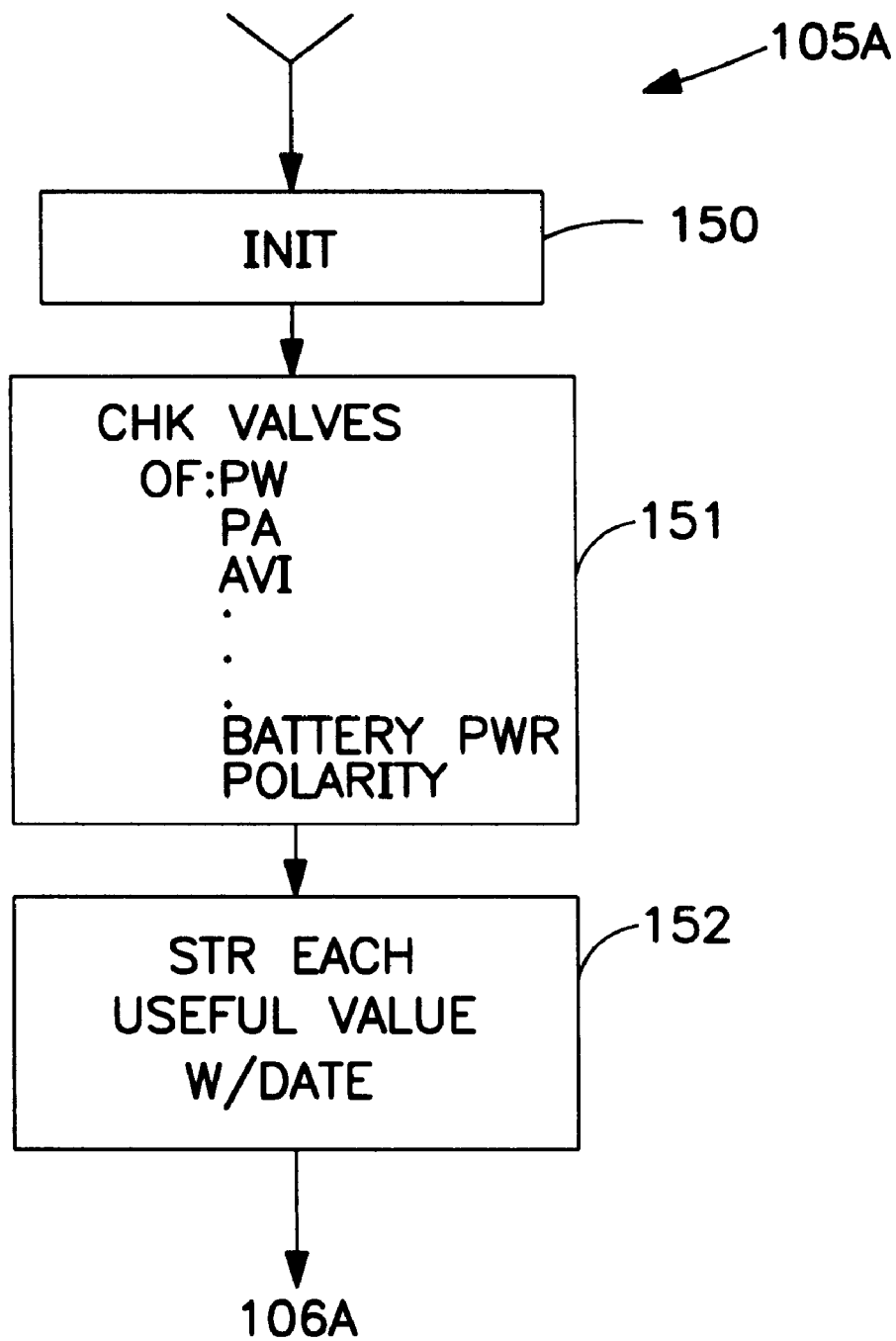
FIG. 6 is a flow chart of warranty monitor date storage activities.

In FIG. 6 the use of implant detection can initiate 150 a program 105a to store values of initial conditions. Here the values of pulse width and amplitude (PW and PA) and atrioventricular interval (AVI), Battery power (impedance, voltage or a combination), lead polarity, and the like are determined and stored 151. A lookup table (not shown) can provide an estimated useful life projection and a warranty date established based on this data. This could generate a date that the device stores 152, which could operate as the warranty date for the device. Alternatively, different programs can be run based on this information with a set of cut off or change over dates distributed based upon the projections and the doctor's therapy recommendations, experimental regimens or even in accord with payment plans if so desired.

Figure 7:
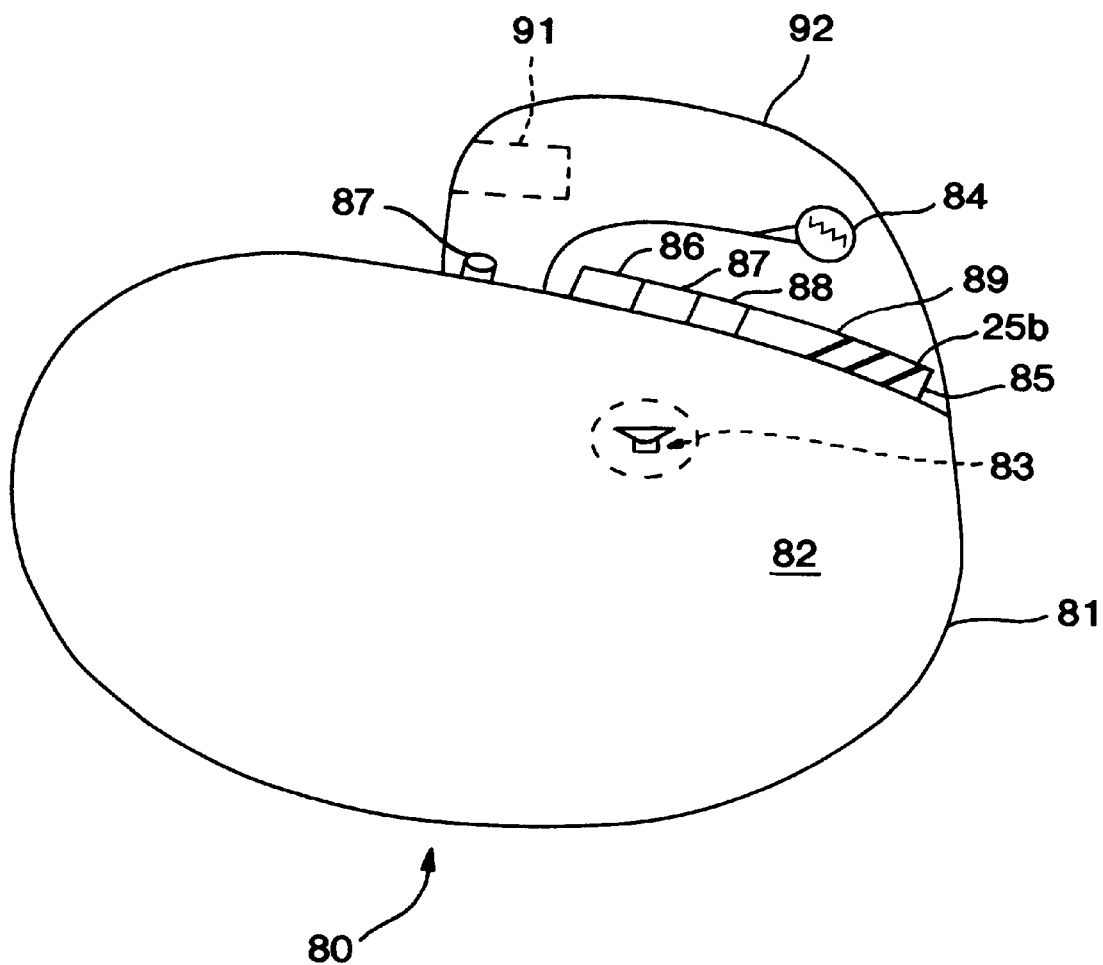
FIG. 7 is a side view of one inventive connector block for use an on IMD shown as a part thereof in accord with one aspect of the invention.

FIG. 7 shows a mechanical design of a pacemaker 82 having various indicator features and sensors for detecting and displaying characteristics of the device at implant. The connector block 92 has a lead bore 91 therein for connecting to a medical electrical lead. An optical sensor 84 could be used to indicate to the device it's transitional state as well as perhaps for sensing oxygen levels of blood after implant. A simple LED 87 could signal a leads connected or not status to the doctor before the device is implanted into the pocket but while connected to the leads. A strip of LCD indicators 85–89 could provide additional information in accord with a pre arranged code. Stripes or text on a portion of the LCD display could be used as in 85b to show battery charge status. Certainly a speaker 83 could be used to supplement the information display chosen for the device.

Figure 8:
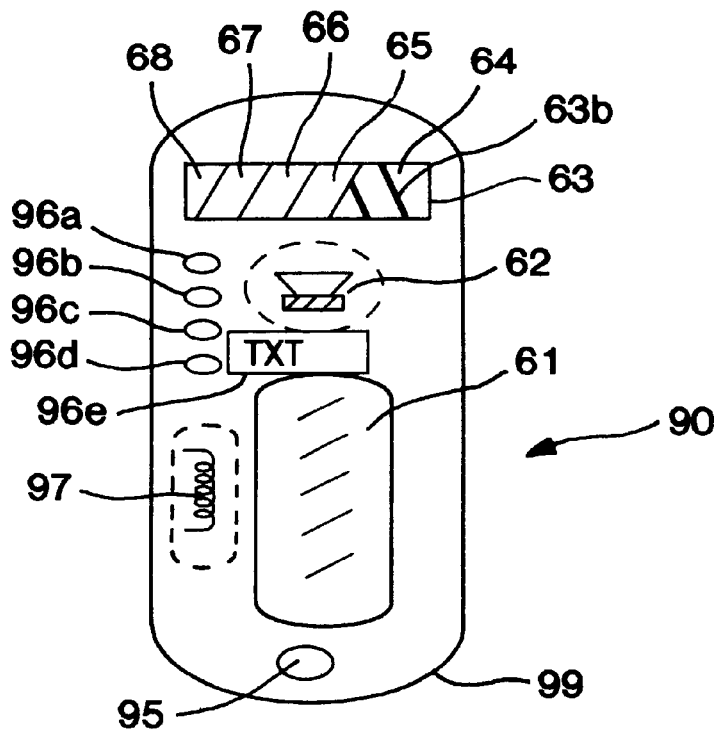
FIG. 8 is a frontal view of an activator for use to trigger operating room communications with the implantable device of this invention and to indicate implant status.

It is believed that a similar set of display features on an activator would be preferable to the display on the implantable device itself, and such is illustrated in FIG. 8. The activator 90 could communicate via a telemetry antenna 97 with the implant. Here the display strip is in parts 62–68, and a multiplicity of LEDs are shown, 96a–d. A separate LCD display for text 96e is also provided and a speaker 62 could also be useful. A push-button 61 for activation is included.

Figure 9:
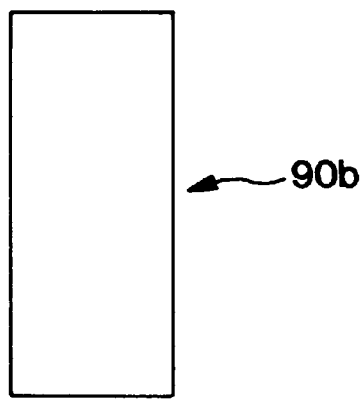
FIG. 9 is an illustration of a simple magnet, operative to perform some of the functions of the activator in accord with this invention.

The simplest method for communicating with an implant is through bringing a bar magnet as in 90b of FIG. 9 into proximity with the IMD, setting a magnetometer or reed switch to a position to generate a report on its status.

Cold Temperature Reset Embodiments.

One of the problems with implantable medical devices which use batteries for power is inherent in the stresses introduced by shipping the devices. Typically, modern aircraft fly at 10,000 meters, potentially subjecting cargoes to temperatures of near −40 degrees (F or C). Also, in automobile trunks or trucks in outdoor temperatures of similar extremes, the device battery may simply have impedance levels much higher and voltage much lower than acceptable for operation of the implantable device.

Accordingly, it is important to not compromise the ability of the implantable device to recognize true ERI conditions and to enable the device to reset ERI and POR/PIR conditions if they are set by the device itself due to environmental conditions prior to implant.

Figure 11:
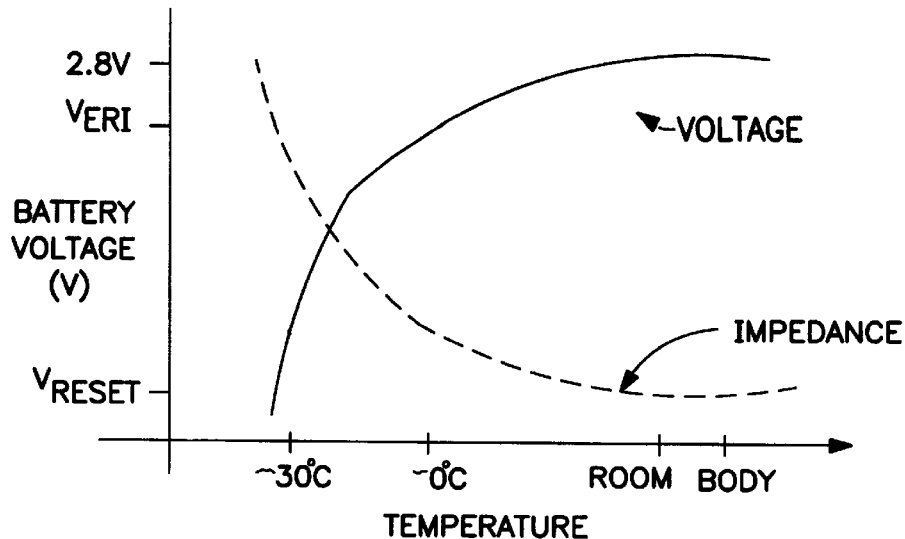
FIG. 11 is a graph of battery voltage versus temperature.

The characteristic impedance curve and voltage curve for the typical Lithium Iodine (LiIo) battery is seen in FIG. 11. A typical IMD voltage of reset is about 1.7 Volts, at which time the device (the IMD) should undergo electrical reset. Prior. to the extreme temperature being reached, near 0 degrees C, the voltage of ERI (typically 2.5 to 2.6 V) is reached. However when the device is rewarmed to room temperature, the voltage and impedance values return to normal. In most devices, this simply means the user/operating room doctor must reprogram the device to reset either the ERI (which means 'Elective Replacement Indicator' condition flag is, set) or POR (which means 'Power on Reset' or PIR, 'Power Interrupt Reset,' meaning a nearly complete loss of power was noted by the device and a reset condition flag was set) condition that has occurred. In our preferred embodiments, we check this condition of ERI and POR/PIR automatically while checking for whether the device is implanted and the device then automatically clears the conditions itself.

Figure 12:
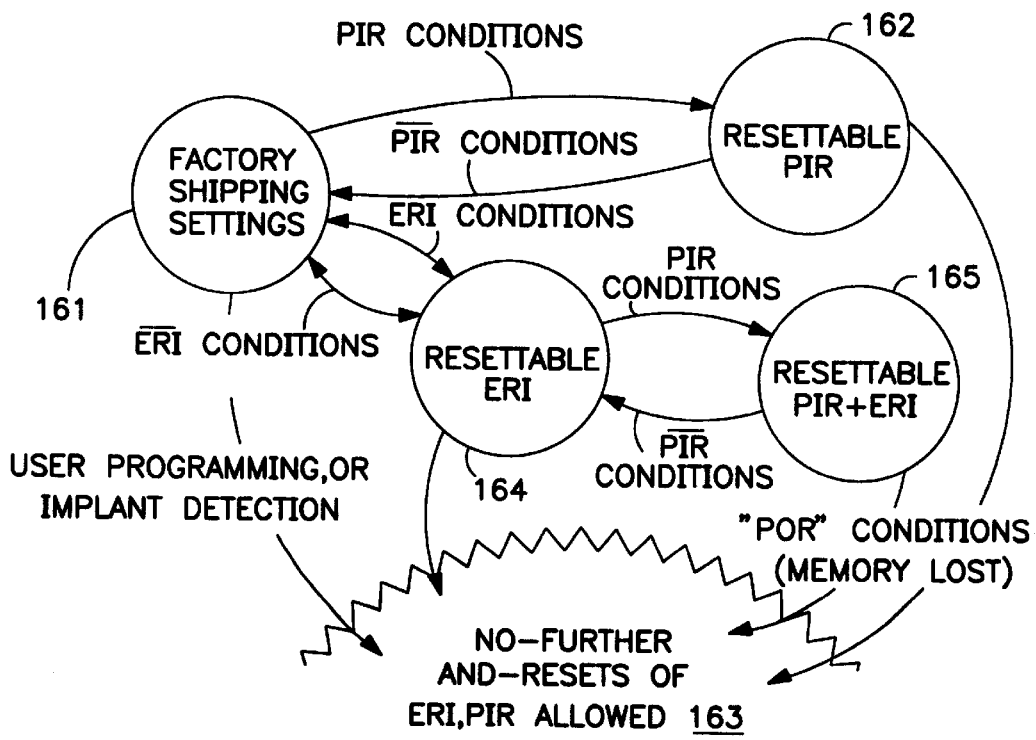
FIG. 12 is a state diagram of ERI and PIR/POR settings.

FIG. 12 indicates what states are available and the transitions between them related to PIR/POR and ERI conditions. The circles indicate the states and the arrows indicate the transitions between states in the state diagram 160. In the factory shipped state 161 the device can through being exposed to cold reach PIR conditions to achieve a resettable PIR state 162, but when programmed or after having implant detection without finding PIR, it cannot be reset from state 163. Likewise in states 164 and 165 the PIR and ERI conditions are resettable. In all resettable states, the factory shipping conditions can be restored, but not if state 163 is achieved.

There are some limits which may not be apparent from FIG. 12. The POR condition is generally harder to achieve than a PIR condition and causes loss of memory including possible loss of data from NV or LVRAM. It occurs after PIR at lower temperatures. Also, since the auto reset of the ERI and PIR/POR conditions is desired only while the device is in shipping or storage, the occurrence of implant detection must disable the auto reset capability. Finally if a user initiated programming of the device occurs, this is also noted and further auto resets of the ERI and PIR should also be disabled. It may be allowed to reset with programming if a large electromagnetic disturbance caused the ERI or POR/PIR condition, but this invention does not address that concern.

Figure 13:
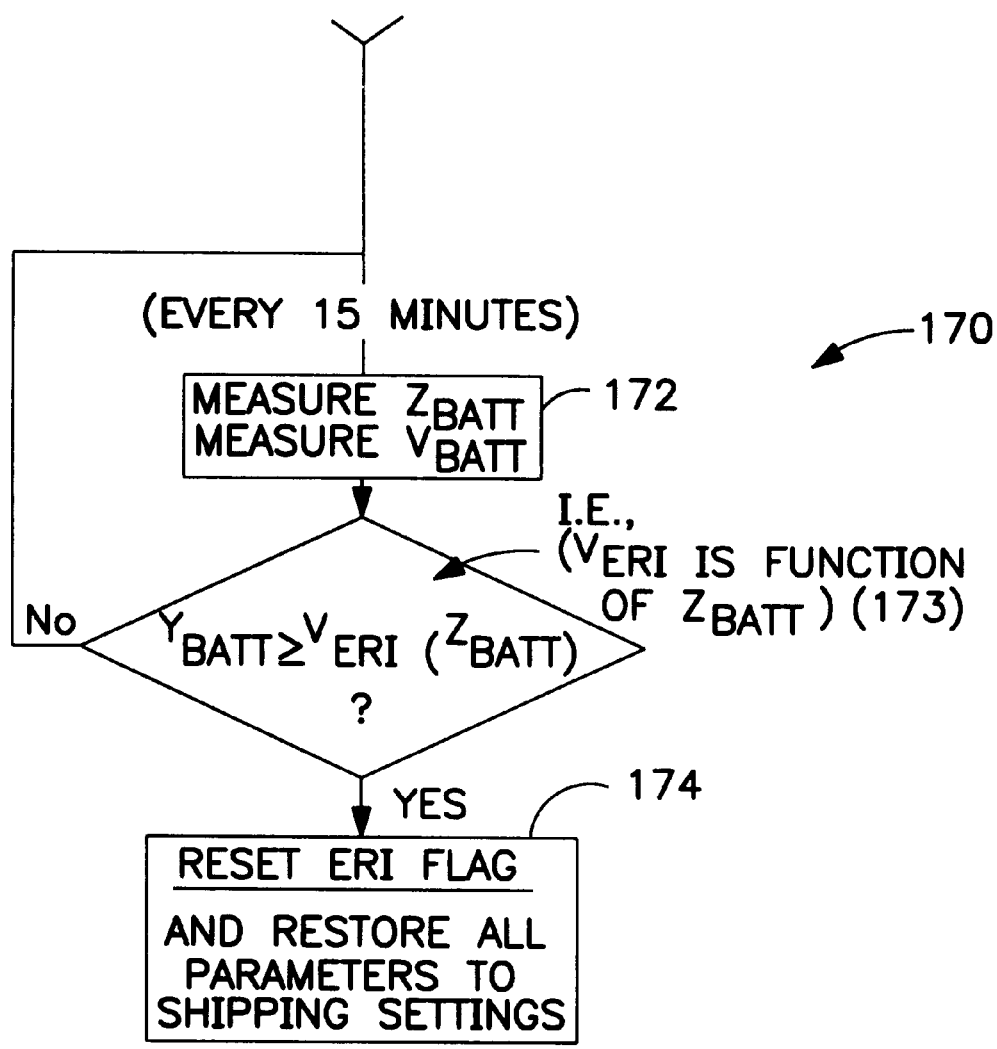
FIGS. 13 and 14 are flow charts describing device functioning in accord with preferred embodiments.
Figure 14:
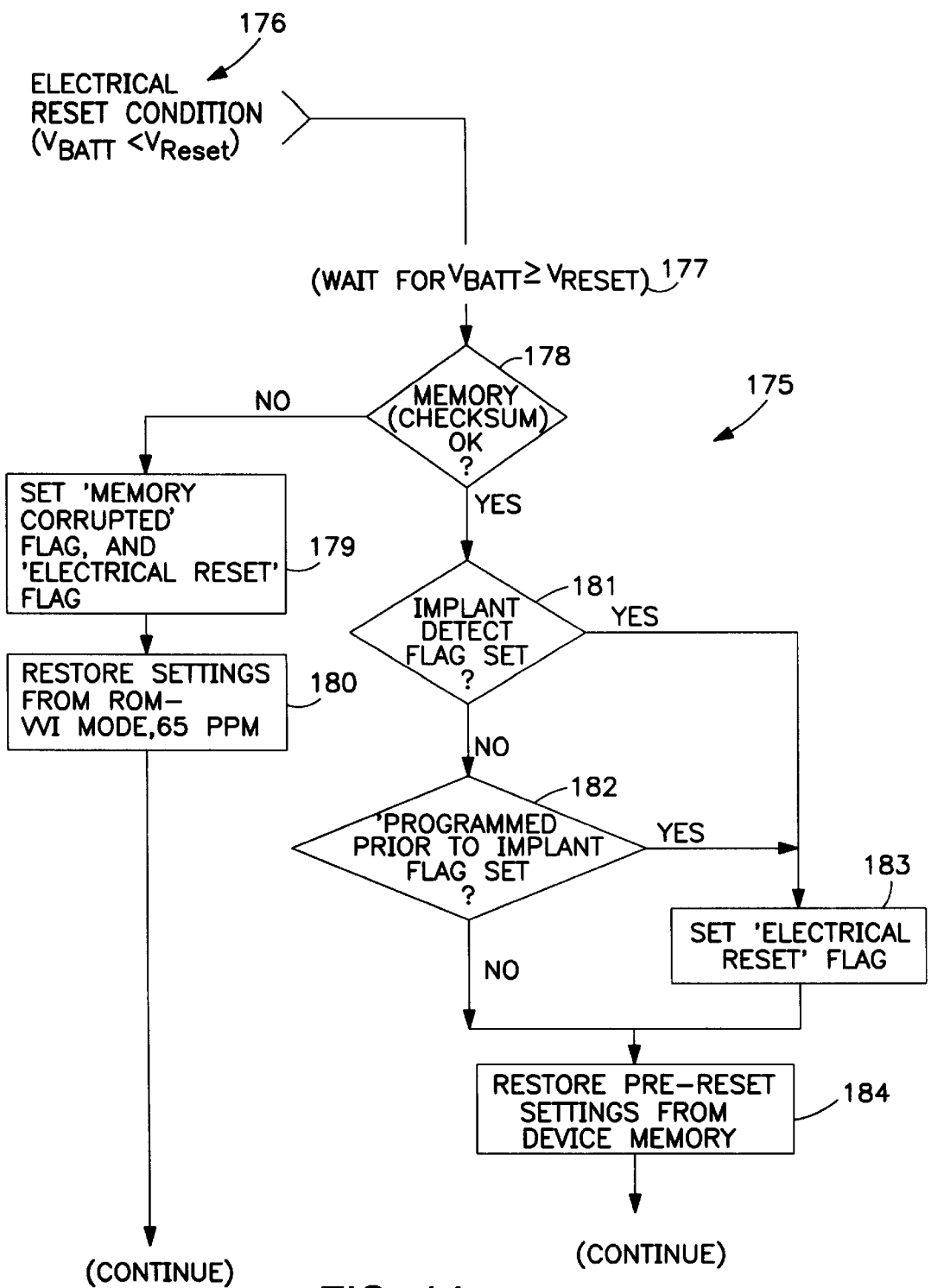

Refer to FIGS. 13 and 14 to discern the details of the operation of the cold temperature auto reset for ERI and POR/PIR, respectively. Note that it is desirable to poll the battery more often for purposes of resetting ERI than for setting it, (e.g., for each 15 minutes rather than every 3 hours, typically) since there may be only a short time between removal of the device from a cold storage condition and implant in the operating room. Therefore auto reset of the ERI should be prompt.

In process 170 (FIG. 13), the condition is in a resettable ERI state (like 164 from the state diagram 160 of FIG. 12). The device in such a state will at a regular interval or based on a trigger (here we prefer a simple 15 minute interval) measure the impedance and voltage of the battery (step 172). If the battery voltage or impedance is not an appropriate function of battery impedance or voltage (step 173), the device waits again for the period to remeasure these parameters. If it is an appropriate function, here shown as the target value for the battery being greater than the measured value of the battery, then the program or process 170 moves on to step 174 and resets the ERI flag in memory so that all shipping parameter settings can be restored.

In the process 175 (FIG. 14), where the start condition is one where the battery has not yet come out of the condition of providing more voltage than the set value for $V_{RESET}$, (stage 176) the device simply does nothing (step 177) waiting for the battery to produce a voltage sufficient to begin testing. Step 178 provides a memory test which in step 179 responds to a corrupted memory condition. In such a state, the non volatile memory settings are restored and a limited functionality is imposed on the IMD in step 180. The device will continue to function that way for the remainder of its useful life unless reprogrammed.

If the memory is OK, the implant detect routine suitable for the device may be initiated. In our preferred embodiment this is described with respect to FIG. 3. However, the tests 181 and 182 for whether the device has entered state 163 must first be performed, and if failed, the flag indicating that no automatic resets from ERI or PIR are allowed. After the tests the device restores the pre set settings to working memory 184 and continues as appropriate.

Preferred ERI mechanism

Typically, with IMDs such as pacemakers, the device should be able to perform some minimal level of functionality as the battery life comes to a close for a time period sufficiently long to avail the person with the implant of a chance to receive a substitute device, a recharge, a new battery or some similar accommodation. Typically, for example, the data logging functions and other non essential features can be shut down to permit this. In the cardiac pacemaker, for example, the goal is to provide the device with a minimum of 90 days additional life support services, for example VVI pacing at 65 ppm before the device has insufficient power to provide consistent and continuous pacing and sufficient amplitude to assure capture. This mode of power saving should be reset, preferably as described above if the ERI condition is not due to a failing battery. For the battery losing power, we have found a way to be more certain of the remaining life of the device, regardless of the duty cycle or current drain curve under which it may have been operating. The problem was that if the device was called upon to expend more than the expected amount of energy in a given period of time, the device would drain its battery more quickly than expected, and with the LiIo batteries commonly used, the voltage level or impedance level is used to determine the extant reserves of battery life. We have found that by having an adaptive target voltage based on a measured change in impedance, we can extend the life of devices that require more than the optimum duty cycle or typical current drain. We could also have an adaptive impedance target based on a measured voltage, (only reversing the curves, of course) to accomplish the same thing.

For reference regarding relations between characteristics of battery life and voltage and impedance (internal resistance in the text), the reader is recommended to the Handbook of Batteries, second edition, by David Linden, published by McGraw Hill, copyright 1995, ISBN 0-07-037921-1, incorporated by reference hereinto in its entirety.

Refer now to FIG. 4a, in which the voltage curve is plotted against time for a typical pacemaker battery. The time is between 3 and 5 years before the $V_{ERI}$ (Voltage trigger point for ERI) point is reached, typically. The sporadic nature of battery usage in an IMD is thus smoothed out of the curve over this period of time.

Lithium Iodine batteries exhibit significant internal resistance, even early in life. This means that the voltage discharge characteristic of the battery is a function of current drain. The battery voltage, at a given point in its discharge will be lower at higher current drain (higher device duty cycle, larger amplitude pacing pulses, and so forth). See FIG. 4b, which describes five voltage droop curves with varying levels of current drain. Note the $V_{ERI}$ point along the curves is closer to the totally discharged capacity percentage as the current drain is less.

At low to moderate current drains, the point along the capacity/voltage curve at which the remaining capacity can supply 90 days at VVI 65 ppm for the pacemaker (or whatever the ERI function modality of the IMD is) is desirable. We consider this the ideal point at which the ERI (flag or other indicator) should be set. However, for the curves to the left (those showing higher current drain), the $V_{ERI}$ point is reached very early in life, when there is still significant battery capacity left. That is, at low current drain levels, the characteristic of an earlier ERI for higher current is beneficial since to achieve the desired 90 days between ERI condition and erratic delivery of therapy, the ERI must be tripped earlier in order to provide the required post ERI battery capacity at a higher current drain.

The curve follows this equation:

$$DT=DQ/I$$

That is, the change in time equals the change in capacity (Q) divided by Current Drain(I)

Therefore, the value of DQ=I times DT, where DQ is the required battery capacity between ERI and onset of erratic performance of the device, and DT is the desired ERI to erratic performance time.

Therefore, to treat the problem of reaching $V_{ERI}$ at an undesirable point too early in time under conditions of high current drain, we define the ERI voltage level $V_{ERI}$ as a function of battery depletion. Specifically we employ a lower $V_{ERI}$ earlier in the battery life and later raise it.

A preferred situation solution is seen and described with reference to FIGS. 4b and 4c where the Q threshold is measured and used to determine when to set the $V_{ERI}$ to a level more useful for low to moderate current drain situations.

A number of alternative preferable embodiments is mentioned, but the simplest one shown in these figures is currently most preferred. For example, we could track the slope of the discharge capacity curve and modify the $V_{ERI}$ level adaptively as a function of that slope. Alternatively we could be measuring the voltage as the trigger curve and use the impedance as the ERI indicator.

In any event, we describe in FIG. 4c a two tiered $V_{ERI}$ function. $V_{ERI}(Q)=\{V_{ERI},2$ if $Q<=Q_{THRESH}$, and $V_{ERI},1$ if $Q>Q_{THRESH}\}$ [$Q_{THRESH}$ being the threshold discharge capacity, of course.] Since for Lithium Iodine Batteries, the AC Battery impedance in monotoncally increasing function of the discharged battery capacity, we prefer to implement the $V_{ERI}$ function as an equivalent function of battery impedance (Z), as shown in FIG. 4d.

Measuring battery voltage and impedance in IMD's is not new. See for example U.S. Pat. No. 5,661,393 (Sengupta) and U.S. Pat. No. 4,390,020 (Herpers), U.S. Pat. No. 5,402,070 (Shelton et al.), U.S. Pat. No. 5,137,020 (Wayne et al.), U.S. Pat. No. 4,259,639 (Reniere) and U.S. Pat. Nos. 4,231,027 and 4,324,251 (Mann, and Mann et al.), all of which are incorporated by reference in their respective entireties. the usefulness of battery impedance was described in Nappholz et al., U.S. Pat. No. 4,448,197 and Blaser in U.S. Pat. No. 4,290,429 monitored battery depletion taking into account both voltage and internal impedance. These two U.S. patents are also incorporated by reference in their entireties as well. Because of the extensive knowledge in the art, no additional disclosure of the circuit details for measuring impedance are required, and since accommodating the circuit to the plethora of potential devices for which it might be useful is within the skill of the ordinary worker in this field, no further details are needed.

Figure 10:
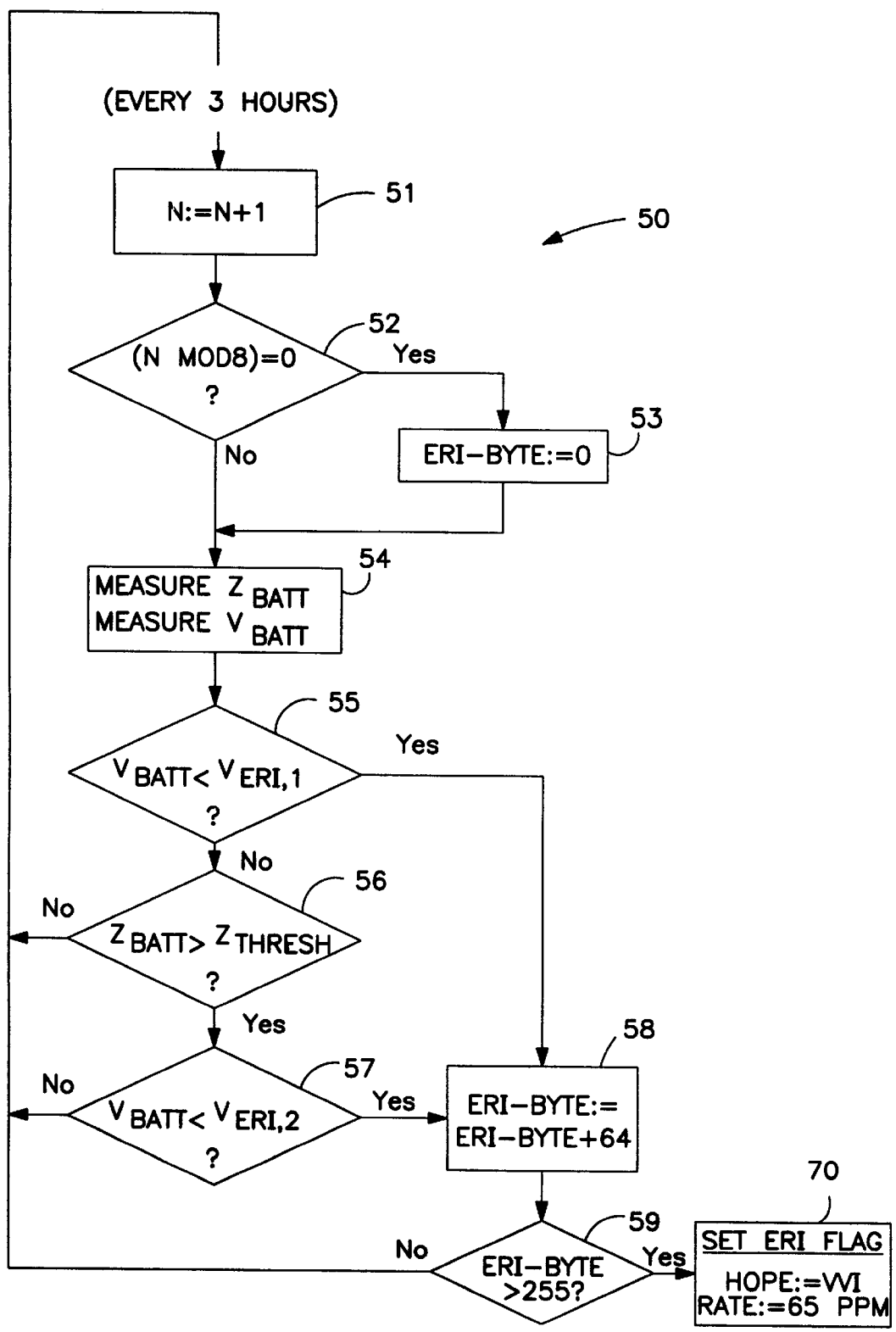
FIG. 10 is a flow chart for determining $V_{ERI}$ (the voltage threshold for setting an Elective Replacement Indicator).

Referring now to FIG. 10 in which a flow chart of the preferred embodiment use of at least two $V_{ERI}$ levels is described the process 50 for determining ERI status preferably operates continuously once the IMD is in normal operation. In FIG. 10 we illustrate that we prefer three hour interval updates, but other times could be chosen, as could consistent trigger events. We first set a counter 51. If it is reset, we take the YES path, but if not, we take the NO path. In our preferred embodiment we use Nmod8 since there are eight 3's in 24. So when N=0, 8, 16, 24 . . . , another day has gone by. We could use anything that would give us a repetition at a daily or other selected time period reiteration. On the YES path, step 53, we set the ERI_BYTE to zero before going on to measure the battery characteristics at step 54. This setting will be used in step 58. In our preferred embodiment this is a byte variable that counts by 64. When it counts up four times, we set the ERI flag, indicating that sufficient time in ERI condition has elapsed to be certain that an ERI condition is present.

After measuring the battery at step 54, we confirm that the voltage of the battery is not less than $V_{ERI},1$. If it is, then we count up the ERI_BYTE counter in step 58, otherwise, we confirm that the impedance and battery voltage is appropriate with respect to the battery impedance warning threshold and VERI,2 levels.

This algorithmic process defined by FIG. 10 is but one of numerous ways to do this, and because of its simplicity is presently preferred. However, if the reader wanted to adjust the level of VERI,1 and VERI,2 according to a table of battery impedance levels over time, a moving VERI could be employed instead of just two preset levels. Or the reader could use such a table of impedance levels over time to simply adjust the impedance threshold in step 56 (or the voltage threshold in step 55), on a sloping curve that goes up in value over time.

From the foregoing detailed description of specific embodiments of the invention, it should be apparent that an automatic implantable device having certain power conservation and implant recognition features has been described through specific embodiments in some detail. This has been done only to illustrate various aspects of the invention, and is not intended to be limiting with respect to the scope of the invention. It is contemplated that various alterations, substitutions, and or modifications, including but not limited to those specifically discussed herein, may be made to the disclosed embodiment without departing from the spirit and scope of the invention, as defined in the appended claims.

What is claimed is:

1. An Implantable Medical Device (IMD) operable in a low power mode and a higher (more consumptive of battery capacity) power mode, and having a battery power source, means to measure the voltage of the battery power source and means to condition the device to a low power operating mode when the battery power source as measured by said means to measure indicates a voltage below a threshold voltage, further comprising a means for resetting said IMD automatically to restore said higher power mode of operation, said means for resetting said IMD including a checking means to prevent resetting if a user has programmed any function of the IMD.

2. An automatic implant detection system for use in an Implantable Medical Device (IMD), said IMD being operable in low power and high power modes, said IMD comprising a power source, measuring means to measure the voltage of the power source, and means to condition the IMD to the low power mode when the power source as measured by the measuring means indicates the power source voltage is below a threshold voltage, said IMD further comprising resetting means for resetting said IMD automatically to restore said high power mode, the automatic implant detection system comprising:

means for producing an implant detection signal indicating implant has been detected if implant has occurred; and checking means to prevent automatic resetting by the resetting means if said signal indicates implant has been detected.

3. An Implantable Medical Device (IMD) operable in a low power mode and a higher (more consumptive of battery capacity) power mode, and having a battery power source, means to measure the impedance of the battery power source and means to condition the device to a low power operating mode when the battery power source as measured by said means to measure indicates an impedance above a threshold impedance, further comprising a means for resetting said IMD automatically to restore said higher power mode of operation, and automatic implant detection means for determining whether the IMD has been implanted and for controlling said means for resetting based on the determination.

4. An IMD as set forth in claim 3 wherein said means for resetting comprises a checking means to prevent resetting if a user has programmed any function of the IMD.

5. An IMD as set forth in claim 3 wherein said automatic implant detection means includes means for producing a signal indicating implant has been detected if implant has occurred, and wherein said means for resetting comprises a checking means to prevent automatic resetting if said automatic implant detection means has produced said signal indicating implant has been detected.

6. An IMD as set forth in any of claim 1, or 2–5 further comprising a programmable memory and means for determining if said programmable memory has been corrupted and for producing a memory corrupted signal indicating that said programmable memory has been corrupted if such is true, and still further comprising means for checking for said memory corruption signal operable to prevent restoration of higher power functioning of said IMD on the detection of said memory corruption signal.

7. An IMD as set forth in any of claim 1 or 3 further comprising a programmable memory and means for determining if said programmable memory has been corrupted and for producing a memory corrupted signal indicating that said programmable memory has been corrupted if such is true, and still further comprising means for checking for said memory corruption signal operable to prevent restoration of higher power functioning of said IMD on the detection of said memory corruption signal and yet further comprising means to prevent automatic resetting of a signal indicating that a condition of low battery power has occurred, operable only on one or both of two conditions, if said IMD has received programming from a user or if the IMD has detected that it has been implanted.

8. A method for automatically resetting an Elective Replacement Indicator (ERI) condition within an Implantable Medical Device (IMD) comprising the steps of:

iteratively measuring either the impedance or the voltage of a battery;

comparing the measurement to a predetermined value;

determining whether the IMD has been implanted; and selectively generating a signal to reset an existing indicator of ERI based on results obtained in said comparing step and said determining step.

9. A method of preventing an automatic resetting an existing indicator signal showing a low power condition in an Implantable Medical Device (IMD) comprising;

upon coming out of a low power condition examining the contents of memory locations and checking the values therein to determine if said memory was corrupted during the low power conditions, if the memory was corrupted, terminating further ability of the IMD to reset the indicator signal, if the memory was not corrupted, determining whether the IMD has been implanted, and if so, terminating further ability of the IMD to automatically reset the indicator signal, else, allowing the IMD to reset the indicator signal.

10. A method of preventing an automatic resetting an existing indicator signal showing a low power condition in an Implantable Medical Device (IMD) comprising;

upon coming out of a low power condition examining the contents of memory locations and checking the values therein to determine if said memory was corrupted during the low power conditions, if the memory was corrupted, terminating further ability of the IMD to reset the indicator signal, if the memory was not corrupted, determining whether the IMD had been programmed by a user, and if so, terminating further ability of the IMD to automatically reset the indicator signal, else, allowing the IMD to reset the indicator signal.

11. A method of preventing an automatic resetting an existing indicator signal showing a low power condition in an Implantable Medical Device (IMD) comprising;

upon coming out of a low power condition examining the contents of memory locations and checking the values therein to determine if said memory was corrupted during the low power conditions, if the memory was corrupted, terminating further ability of the IMD to reset the indicator signal, if the memory was not corrupted, determining whether the IMD had been programmed by a user, and if so, terminating further ability of the IMD to automatically reset the indicator signal, and determining whether the IMD has been implanted, and if so, terminating further ability of the IMD to automatically reset the indicator signal, else, allowing the IMD to reset the indicator signal.

* * * * *